(12) United States Patent
Hsu et al.

(10) Patent No.: US 6,458,997 B2
(45) Date of Patent: *Oct. 1, 2002

(54) CONTINUOUS HYDROLYSIS PROCESS FOR THE PREPARATION OF 2-HYDROXY-4-METHYLTHIOBUTANOIC ACID

(75) Inventors: Yung C. Hsu; Thomas F. Blackburn, both of Chesterfield; Paul F. Pellegrin, St. Louis; Allen H. Kranz, St. Charles; James M. Willock, Ballwin, all of MO (US)

(73) Assignee: Novus International, Inc., St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 09/748,067

(22) Filed: Dec. 22, 2000

Related U.S. Application Data

(62) Division of application No. 09/165,806, filed on Oct. 2, 1998, now Pat. No. 6,166,250, which is a division of application No. 08/876,011, filed on Jun. 13, 1997, now Pat. No. 5,998,664, which is a continuation of application No. 08/477,768, filed on Jun. 7, 1995, now abandoned.

(51) Int. Cl.$^7$ .............................................. C07C 51/42
(52) U.S. Cl. ....................................................... 562/581
(58) Field of Search ................................. 562/580, 581

(56) References Cited

U.S. PATENT DOCUMENTS

| | | |
|---|---|---|
| 2,458,236 A | 10/1949 | Gresham et al. |
| 2,542,768 A | 2/1951 | Gresham et al. |
| 2,557,920 A | 6/1951 | White |
| 2,564,105 A | 8/1951 | Gresham et al. |
| 2,642,459 A | 6/1953 | White |
| 2,688,038 A | 8/1954 | Merner |
| 2,745,745 A | 5/1956 | Blake et al. |
| 2,938,053 A | 5/1960 | Blake et al. |
| 2,946,818 A | 7/1960 | Anagnostopoulos |
| 3,773,927 A | 11/1973 | Cummins |
| 3,968,152 A | 7/1976 | Sze et al. |
| 4,233,235 A | 11/1980 | Camden et al. |
| 4,310,690 A | 1/1982 | Cummins |
| 4,311,803 A | 1/1982 | Smith et al. |
| 4,524,077 A | 6/1985 | Ruest et al. |
| 4,677,224 A | 6/1987 | Commeyras et al. |
| 4,912,257 A | 3/1990 | Hernandez et al. |
| 5,068,383 A | 11/1991 | Bourgoin et al. |
| 5,244,590 A | 9/1993 | Chung et al. |
| 5,250,611 A | 10/1993 | Baumgartner et al. |
| 5,420,304 A | 5/1995 | Verser et al. |
| 5,856,567 A | 1/1999 | Hsu et al. |
| 5,998,664 A * | 12/1999 | Hsu et al. .................... 562/580 |
| 6,166,250 A * | 12/2000 | Hsu et al. .................... 562/580 |
| 6,268,531 B1 * | 7/2001 | Hsu et al. .................... 562/580 |

FOREIGN PATENT DOCUMENTS

| | | |
|---|---|---|
| DE | 4236058 | 4/1994 |
| EP | 143 100 A2 | 5/1985 |
| GB | 915193 | 1/1963 |
| JP | 57-82339 | 5/1982 |
| RO | 72031 | 3/1981 |
| RO | 104950 | 12/1994 |
| WO | WO 00/02852 A1 | 1/2000 |

OTHER PUBLICATIONS

Denbigh, K., "Chemical Reactor Theory". Cambridge at the University Press, No month provided 1965, Chapters 2–4, pp. 38–124.

Trambouze et al., "Continuous Stirred Tank Reactors", A.I.Ch.E. Journal, No month provided 1959, pp. 384–390.

Cholette, et al., "Optimum . . . Conditions," The Can. J. of Chem. Eng., No month provided 1961, pp. 192–198.

Cholette, et al., "Performance of Flow Reactors . . . Mixing", The Can. J. of Chem. Eng., No month provided 1960, pp. 1–18.

* cited by examiner

*Primary Examiner*—Rosalynd Keys
(74) *Attorney, Agent, or Firm*—Senniger, Powers, Leavitt & Roedel

(57) ABSTRACT

A continuous process for the preparation of 2-hydroxy-4-methylthiobutanoic acid which includes introducing sulfuric acid into a first reactor including a continuous stirred tank reactor and introducing 2-hydroxy-4-methylthiobutanenitrile into the first reactor. 2-hydroxy-4-methylthiobutanenitrile is continually hydrolyzed within the first reactor to produce an intermediate aqueous hydrolysis solution containing 2-hydroxy-4-methylthiobutanamide. The intermediate aqueous hydrolysis solution is continuously introduced into a plug flow reactor. 2-hydroxy-4-methylthiobutanamide is continually hydrolyzed within the plug flow reactor to produce an aqueous hydrolyzate product solution containing 2-hydroxy-4-methylthiobutanoic acid. 2-hydroxy-4-methylthiobutanoic acid is recovered from the aqueous hydrolyzate product solution.

7 Claims, 6 Drawing Sheets

CONTINUOUS HYDROLYSIS PROCESS FOR THE PREPARATION OF 2-HYDROXY-4-METHYLTHIOBUTANOIC ACID

CROSS REFERENCE TO RELATED PATENT APPLICATIONS

This application is a divisional of U.S. patent application Ser. No. 09/165,806, filed Oct. 2, 1998, now issued as U.S. Pat. No. 6,166,250, which is a divisional of U.S. patent application Ser. No. 08/876,011, filed Jun. 13, 1997, now issued as U.S. Pat. No. 5,998,664, which is a filewrapper continuation of U.S. patent application Ser. No. 08/477,768, filed Jun. 7, 1995, now abandoned.

BACKGROUND OF THE INVENTION

This invention relates to the preparation of 2-hydroxy-4-methylthiobutanoic acid and more particularly to an improved process for preparing an aqueous solution comprising 2-hydroxy-4-methylthiobutanoic acid.

2-hydroxy-4-methylthiobutanoic acid, commonly referred to as the hydroxy analog of methionine and also known as 2-hydroxy-4-methylthiobutyric acid or HMBA, is an analog of the essential amino acid methionine. Methionine analogs such as HMBA are effective in supplying methionine for nutritional uses, particularly as a poultry feed supplement. To efficiently produce feed supplements containing HMBA, the hydrolysis must be sufficiently complete.

HMBA has been manufactured by various processes involving hydrolysis of 2-hydroxy-4-methylthiobutanenitrile (also known as HMBN or 2-hydroxy-4-methylthiobutyronitrile and hereinafter "HMEN" or "nitrile"). HMBA has been produced as a racemic D,L-mixture by hydrolyzing HMBN with a mineral acid, precipitating the acid residue by addition of an alkaline earth hydroxide or carbonate, and recovering a salt of HMBA from the aqueous phase by evaporative crystallization, as described, for example, in Blake et al U.S. Pat. No. 2,745,745.

British Patent No. 915,193 describes a process for the preparation of the calcium salt of HMBA in which HMBN is hydrolyzed to HMBA in a continuous back-mixed reactor using a dilute sulfuric acid solution, and HMBA is separated from the reaction liquor by extraction with an ether. Because of the use of a continuous back-mixed reaction system, the process of the British patent may not achieve complete conversion of HMBN or amide intermediate to HMBA. The presence of unreacted material is undesirable where a liquid HMBA product is to be made.

Recently, HMBA has been commercially produced by hydrolyzing HMBN with sulfuric acid to form a high quality hydrolyzate containing HMBA, extracting HMBA from the hydrolyzate, and recovering the HMBA from the extract as described by Ruest et al. U.S. Pat. No. 4,524,077. In the process, HMBN is mixed with sulfuric acid having a strength of between about 50% and about 70% by weight on an organic-free basis at a temperature of between about 25° C. and about 65° C. To control the rate of reaction, the HMBN is preferably added to the acid over a period of about 30 to about 60 minutes. Under the preferred conditions, substantial conversion of the nitrile to 2-hydroxy-4-methylthiobutanamide (also known as 2-hydroxy-4-methylthiobutyramide and hereinafter "amide") takes place in a period of between about one-half hour and about one and one-half hours. Thereafter, the amide is converted to HMBA by further hydrolysis at a temperature within the range of between about 70° C. and 120° C. Final hydrolysis of the amide to the acid is carried out in sulfuric acid having an initial strength of between about 30% and about 50% by weight on a organic-free basis. To provide the preferred acid strength, the acid phase is diluted by adding water before heating the reaction mixture. Under conditions of relatively dilute acid strength and increased temperature, the amide is converted to the acid within a period of approximately one and one-half to three hours. In carrying out the hydrolysis, approximately one mole of sulfuric acid per mole of the HMBN feed is used, with an acid excess of 0 to 10%, preferably 0 to 5%, providing satisfactory results. Ruest et al. describe a batch process and state that a batch process is preferred to ensure that the hydrolysis reaction is carried substantially to completion. If a continuous reaction system is utilized, Ruest et al. describe that it should be designed and operated to assure essentially complete conversion. For example, continuous operation could be implemented in a plug flow tubular reactor or cascaded stirred tank system. A single back-mixed reactor is described by Ruest et al. as providing adequate conversion only at residence times that would generally be considered unacceptable for commercial production.

Hernandez et al. U.S. Pat. No. 4,912,257 describes a process in which HMBA is produced by sulfuric acid hydrolysis of HMBN in a single step. HMBN is fed to an acidification vessel where it is mixed with 98% sulfuric acid at an acid/nitrile molar ratio between 0.5 and 2 to form a reaction mixture containing 20–50% by weight sulfuric acid. The mixture is agitated and cooled to 50° C. in a continuous addition loop for 30–60 minutes as the reaction mixture is produced batchwise. The reaction mixture is then fed to a hydrolysis reactor and heated to a temperature of between 60° C. and 140° C. for five minutes to six hours while applying a slight vacuum to the reactor. The process described by Hernandez et al. is said to produce HMBA by hydrolysis of the acidified HMBN solution in a single step unlike the two step hydrolysis processes known in the art.

In order to provide a high quality hydrolyzate solution containing maximum HMBA and minimal nitrile and amide components, high conversion of HMBN and 2-hydroxy-4-methylthio-butyramide to HMBA must be obtained. Batch production of HMBA generally provides high conversion. However, conventional batch processes for producing HMBA have several drawbacks. The productivity of a batch process is limited by batch turnaround time. Additionally, the quality of HMBA hydrolyzate can deviate between batches because reaction conditions can vary as each batch is produced. Filling and emptying of the batch reactor and non-steady state conditions cause vapor emissions which must be treated before release. The equipment required for the prior art processes is costly. Sulfuric acid and water are mixed in an acid dilution tank to form diluted sulfuric acid feed. A heat exchanger is required to remove the heat of dilution that is generated within the tank. The tank, heat exchanger, pump and recirculation loop must be of corrosion resistant construction.

SUMMARY OF THE INVENTION

Among the several objects of the present invention are the provision of an improved process for the preparation of HMBA; the provision of such a process which can be operated in a continuous mode; the provision of such a process which can be operated with high productivity; the provision of such a process which can significantly reduce capital and maintenance costs as compared to conventional processes; the provision of such a process which affords improved control of reaction conditions as compared to conventional batch hydrolysis systems; the provision of such a process which reduces the vapor emissions as compared to conventional batch systems; the provision of such a process which eliminates the need for separate sulfuric acid dilution, in particular, the provision of such a process which can be operated using a concentrated sulfuric acid feed stream without prior dilution; and the provision of such a process which can produce HMBA of consistent quality for use in the preparation of animal feed supplements.

These and other objects are obtained through a process for the preparation of HMBA including introducing sulfuric acid into a first reactor comprising a continuous stirred tank reactor, and introducing 2-hydroxy-4-methylthiobutanenitrile into the first reactor. 2-hydroxy-4-methylthiobutanenitrile is continually hydrolyzed within the first reactor to produce an intermediate aqueous hydrolysis solution containing 2-hydroxy-4-methylthiobutanamide. The intermediate aqueous hydrolysis solution is continuously introduced into a plug flow reactor. 2-hydroxy-4-methylthiobutanamide is continuously hydrolyzed within the plug flow reactor to produce an aqueous hydrolyzate product solution containing 2-hydroxy-4-methylthiobutanoic acid. 2-hydroxy-4-methylthiobutanoic acid is recovered from the aqueous hydrolyzate product solution.

In another embodiment of the invention, 2-hydroxy-4-methylthiobutanoic acid is produced by a process in which 2-hydroxy-4-methylthiobutanenitrile, concentrated sulfuric acid having a strength of between about 70% by weight and about 99% by weight, and water are concurrently introduced into a vessel in which 2-hydroxy-4-methylthiobutanenitrile is hydrolyzed. 2-hydroxy-4-methylthiobutanenitrile is hydrolyzed within the vessel to produce an intermediate aqueous hydrolysis solution containing 2-hydroxy-4-methylthiobutanamide. 2-hydroxy-4-methylthiobutanamide is hydrolyzed to produce an aqueous hydrolyzate product solution containing 2-hydroxy-4-methylthiobutanoic acid. 2-hydroxy-4-methylthiobutanoic acid is recovered from the aqueous hydrolyzate product solution.

Yet another embodiment of the present invention is directed to an apparatus for use in a process for the preparation of HMBA. The apparatus includes a first continuous stirred tank reactor for the continuous hydrolysis of 2-hydroxy-4-methylthiobutanenitrile in the presence of sulfuric acid to produce an intermediate aqueous hydrolysis solution containing 2-hydroxy-4-methylthiobutanamide. The apparatus also includes a plug flow reactor for the continuous hydrolysis of 2-hydroxy-4-methylthiobutanamide with sulfuric acid to produce an aqueous hydrolyzate product solution containing 2-hydroxy-4-methylthiobutanoic acid.

DETAILED DESCRIPTION OF THE PREFERRED EMBODIMENT

Figure 1:
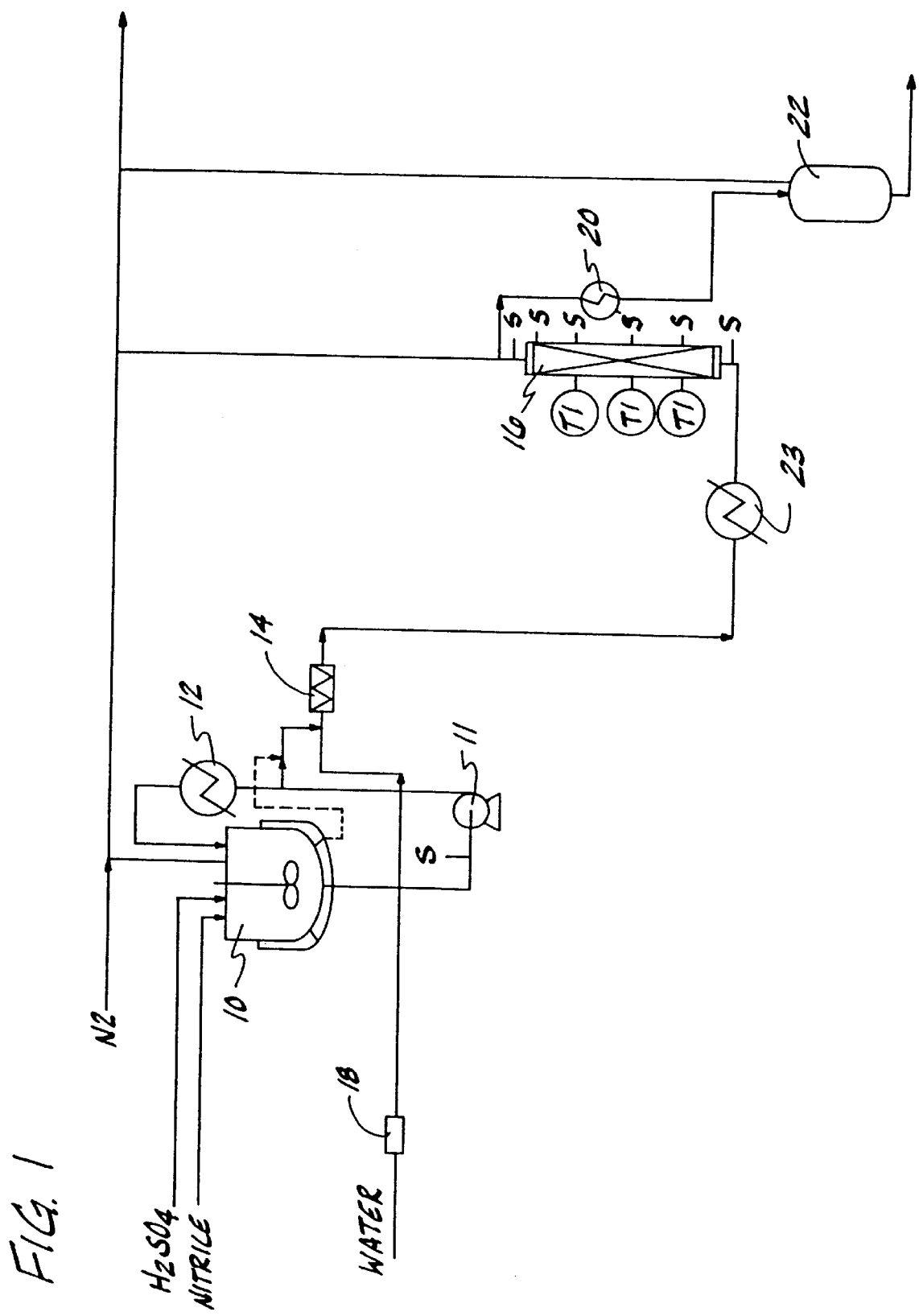
FIG. 1 is a schematic flowsheet of the process of the invention, illustrating continuous manufacture of HMBA from HMBN, water and sulfuric acid.

In accordance with the present invention, a process for the preparation of HMBA is provided in which HMBN is continuously hydrolyzed in the presence of sulfuric acid to form 2-hydroxy-4-methylthiobutanamide (hereinafter referred to as "nitrile hydrolysis"), and the amide is continuously hydrolyzed to form HMBA (hereinafter "amide hydrolysis"). The process is implemented utilizing an apparatus which comprises a first continuous stirred tank reactor (hereinafter "CSTR") for nitrile hydrolysis and a plug flow reactor (hereinafter "PFR") for subsequent amide hydrolysis. The nitrile hydrolysis generates substantial exothermic heat and is, therefore, most efficiently conducted in a CSTR back mixed for heat transfer and temperature control. The amide hydrolysis is less exothermic yet must be brought to completion in order to achieve desired product quality and yield. A PFR has been found to be well suited for the amide hydrolysis because it can be configured to operate without substantial back-mixing, yet provide adequate residence time for the reaction without requiring excessive pressure drop. For example, it has been found that an industrial scale pipeline reactor can be operated at a Reynolds number in excess of about 5000 without excessive pressure drop through the reactor, while producing a hydrolyzate containing less than about 0.1% amide and less than about 0.1% nitrile on an HMBA basis.

More particularly, the invention is directed to an apparatus including a first reactor comprising a first CSTR for receiving sulfuric acid and HMBN feed streams. It has been discovered that concentrated sulfuric acid, water, and HMBN can be concurrently introduced into the first CSTR in order to produce within the CSTR a more dilute effective sulfuric acid strength suitable for hydrolysis of HMBN. Despite the disparate density and viscosity of sulfuric acid and HBMN and the high heat of dilution released when sulfuric acid is diluted with water, HMBN, water and concentrated sulfuric acid can be simultaneously fed into the first CSTR without hindering the hydrolysis of HMBN. The dilution of sulfuric acid within the reactor eliminates the need for separate acid dilution as used in a conventional batch process, reducing cost and maintenance of the hydrolysis system. As the HMBN reacts with water within the CSTR, an intermediate aqueous hydrolysis solution containing 2-hydroxy-4-methylthiobutanamide is formed. The intermediate aqueous hydrolysis solution is then mixed with a heated water stream to provide water for amide hydrolysis and prevent liquid phase separation within the PFR and precipitation of ammonium bisulfate. The diluted intermediate hydrolysis solution may be continuously fed to a second CSTR. Alternatively, the intermediate aqueous hydrolysis solution and the heated water stream can be introduced directly to the second CSTR. A substantial portion of the amide is converted to HMBA in the second CSTR by further hydrolysis to form a finishing reaction solution. The finishing reaction solution is further hydrolyzed in a PFR located downstream of the second CSTR to form an aqueous hydrolyzate product solution containing HMBA. Alternatively, the second CSTR can be bypassed such that the diluted intermediate hydrolysis solution is continuously fed directly to the PFR and hydrolyzed to form the hydrolyzate product solution. It has been discovered that the process of the invention may be operated at high productivity in one or more CSTRs in series together with a PFR finishing reactor. Thus, the capital costs of implementing the process compare favorably with the batch processes previously considered necessary in the art to provide adequate conversion at high productivity.

It has been found that such a continuous hydrolysis process can provide efficient conversion of HMBN to HMBA to produce a high quality hydrolyzate product containing trace amounts of HMBN and 2-hydroxy-4-methylthiobutanamide. In order to produce quality feed supplements containing HMBA, the process of the invention may be operated at high productivity to produce an aqueous hydrolyzate product solution comprising at least about 36 wt. % HMBA, at least about 30 wt. % ammonium bisulfate, at least about 25 wt. % water, up to about 0.05 wt. % amide and up to about 0.05 wt. % nitrile. The HMBA within the aqueous hydrolyzate product solution includes HMBA monomer as well as dimers. In a particularly preferred embodiment of the invention, high conversion is achieved during start up as well as at steady state so that the above described product composition may be consistently produced throughout all process operations.

Ordinarily, the hydrolyzate product produced before steady state conditions are established, for example, during start up, could contain more amide and nitrile than is desired in a high quality HMBN product. It has been discovered that such composition fluctuations can be prevented by operating at a higher acid to nitrile molar ratio during start up in order to establish steady state conditions very rapidly. Presumably, all the acid and HMBA are introduced into the first CSTR reactor, but it would be feasible to divide the acid stream and introduce one portion directly into the PFR. Broadly speaking, therefore, the acid to nitrile molar ratio is based on the cumulative rates at which acid and nitrile are introduced into the process as a whole. Operation at a higher acid to nitrile ratio is achieved by controlling the rate of sulfuric acid flowing into the plug flow reactor so that it is at least stoichiometrically equivalent to the sum of the nitrile and acid flowing into that reactor. For effective control, the acid rate is preferably at least 5% in excess of the rate equivalent to the sum of nitrile and amide. The acid to nitrile molar ratio is between about 1.0 and about 2.0 from start up of the process until steady state is established, preferably between about 1.0 and about 1.5, and most preferably between about 1.15 and about 1.25. After steady state is reached, the acid to nitrile molar ratio is between about 0.7 and about 1.5, preferably between about 0.9 and about 1.2, and most preferably between about 0.95 and about 1.05.

Referring to FIG. 1, 2-hydroxy-4-methylthiobutanamide is continuously generated by the hydrolysis of HMBN in a CSTR 10. At start up of the process, a sulfuric acid feed stream is introduced into the reactor 10 and circulated therein. The sulfuric acid has a strength of between about 50% by weight and about 70% by weight, preferably between about 60% by weight and about 70% by weight.

HMBN is then introduced into the circulating sulfuric acid stream where it reacts with water to form the amide within the aqueous hydrolysis solution. Continuous nitrile hydrolysis occurs as the HMBN and sulfuric acid streams are continuously fed to the aqueous hydrolysis solution within the reactor 10. Sulfuric acid serves as a catalyst and is not consumed in the nitrile hydrolysis reaction. The residence time during which the intermediate aqueous hydrolysis solution is contained within the reactor 10 is between about 20 minutes and about 60 minutes, preferably between about 25 minutes and about 45 minutes. The intermediate aqueous hydrolysis solution produced in the reactor comprises up to about 11 wt. % HMBA, up to about 8 wt. % ammonium bisulfate, at least about 10 wt. % water, at least about 35 wt. % amide and up to about 2 wt. % nitrile. The intermediate aqueous hydrolysis solution preferably comprises between about 5 and about 10 wt. % HMBA, between about 4 and about 8 wt. % ammonium bisulfate, between about 10 and about 15 wt. % water, between about 35 and about 50 wt. % amide and up to about 2 wt. % nitrile, and more preferably, comprises between about 5 and about 8 wt. % HMBA, between about 4 and about 5 wt. % ammonium bisulfate, between about 12 and about 13 wt. % water, between about 40 and about 50 wt. % amide and up to about 1 wt. % nitrile.

The reaction is carried out at a temperature between about 40° C. and about 70° C., preferably between about 60° C. and about 65° C., and at a total pressure of between about 0 and about 15 psig. A pump 11 circulates reacting solution between CSTR 10 and an external heat exchanger 12, in which exothermic heat of reaction is removed by transfer to a coolant. The reactor 10 may also be jacketed to provide additional cooling capacity, and also to provide for heating the contents of the reactor if required during start up.

The liquid level within the reactor 10 is maintained constant by a level controller. Although the liquid level can also be controlled by gravity overflow from the reactor, the hydrolysis system is more easily designed if positive level control is utilized. A level controller is also preferred because the intermediate hydrolysis solution is viscous. Moreover the availability of a level controller allows the working volume and residence time of the reactor be varied at the operator's selection, e.g., to adapt to changes in throughput.

As the intermediate aqueous hydrolysis solution is generated, it exits the reactor 10 and is mixed with a heated water stream in an in-line mixer 14 to form a diluted aqueous hydrolysis solution. The water stream is heated to a temperature of between about 60° C. and about 100° C., preferably between about 70° C. and about 90° C., and, most preferably between about 75° C. and about 80° C. The intermediate aqueous hydrolysis solution is mixed with the heated water stream to prevent separation of the organic and aqueous phases or precipitation of ammonium bisulfate within the PFR. The water stream also further dilutes sulfuric acid within the solution, provides water to be consumed during amide hydrolysis, and reduces the viscosity of the solution. The water stream is introduced at a rate which provides sulfuric acid strength in the diluted aqueous hydrolysis solution of between about 30% and about 50% by weight on an organic-free basis, preferably between about 35% to about 45% by weight, more preferably about 43% by weight.

If the temperature of the diluted aqueous hydrolysis solution is too low for adequate amide conversion, the solution may be brought to the requisite temperature in a preheater 23. Preheating the solution may be necessary, for example, when ambient heat losses are significant. The diluted aqueous hydrolysis solution enters a PFR 16 either directly from the mixer or after being preheated. In the PFR, the small amount of residual HMBN is hydrolyzed to form additional amide and the amide is hydrolyzed to form HMBA. Preferably, the molar ratio of water to amide fed to the PFR is between about 5 and about 10. To maintain turbulence within the PFR and minimize axial backmixing therein, the flow rate of the diluted aqueous hydrolysis solution is operated to maintain suitable velocity within the PFR.

As indicated above, at a given residence time in the PFR, it has been found that conversion may be substantially increased by increasing the acid/nitrile molar ratio in the feed. Experience has shown that in some instances steady state is obtained in about two hours during start up when the acid/nitrile molar ratio is 1.0, yet steady state conditions, and complete conversion, may be obtained almost immediately when the acid/nitrile molar ratio is 1.2. Rapid establishment of steady state conditions enables consistent production of a high quality hydrolyzate product which comprises up to about 0.05 wt. % amide and up to about 0.05 wt. % nitrile upon leaving the PFR 16.

The expense of the excess acid, however, may be prohibitive if an increased acid/nitrile molar ratio is maintained during routine operation of the process after steady state conditions are established. Thus, it is preferable to use an acid/nitrile molar ratio of between about 1.0 and about 1.5, preferably between about 1.15 and about 1.25, only from initial start up until steady state conditions are established in the PFR in order to avoid preparation of off-specification hydrolyzate product during start-up. Such a molar ratio is obtained when the amount of excess sulfuric acid added to the CSTR 10 is between about 10 and about 50% by weight, preferably between about 15 and about 25% by weight, over that stoichiometrically equivalent to the amide and HMBN introduced to the PFR. After steady state is established, the acid/nitrile molar ratio can then be adjusted to, and maintained at, a more cost effective molar ratio of between about 0.7 and about 1.15, preferably between about 0.95 and about 1.05. The preferred steady state molar ratio is obtained when the amount of excess sulfuric acid added to the CSTR 10 is between about 0 and about 15% by weight, preferably between about 0 and about 5% by weight, over that stoichiometrically equivalent to the amide and HMBN introduced to the PFR. The water feed rate into the mixer 14 may be increased to avoid liquid phase separation of organic and aqueous phases when an acid/nitrile molar ratio below 1.0 is used. It has been discovered that operation of the PFR at a high acid/nitrile molar ratio during start up improves conversion of amide to HMBA within the PFR without darkening the color of the hydrolyzate product. Despite the increased severity of reaction conditions provided by a high acid/nitrile ratio, it has unexpectedly been discovered that acid/nitrile molar ratio does not significantly affect hydrolyzate color. Moreover, the high acid to nitrile molar ratio also allows PFR operation at a lower temperature during steady state operation, therefore producing a light colored hydrolyzate product.

Figure 2:
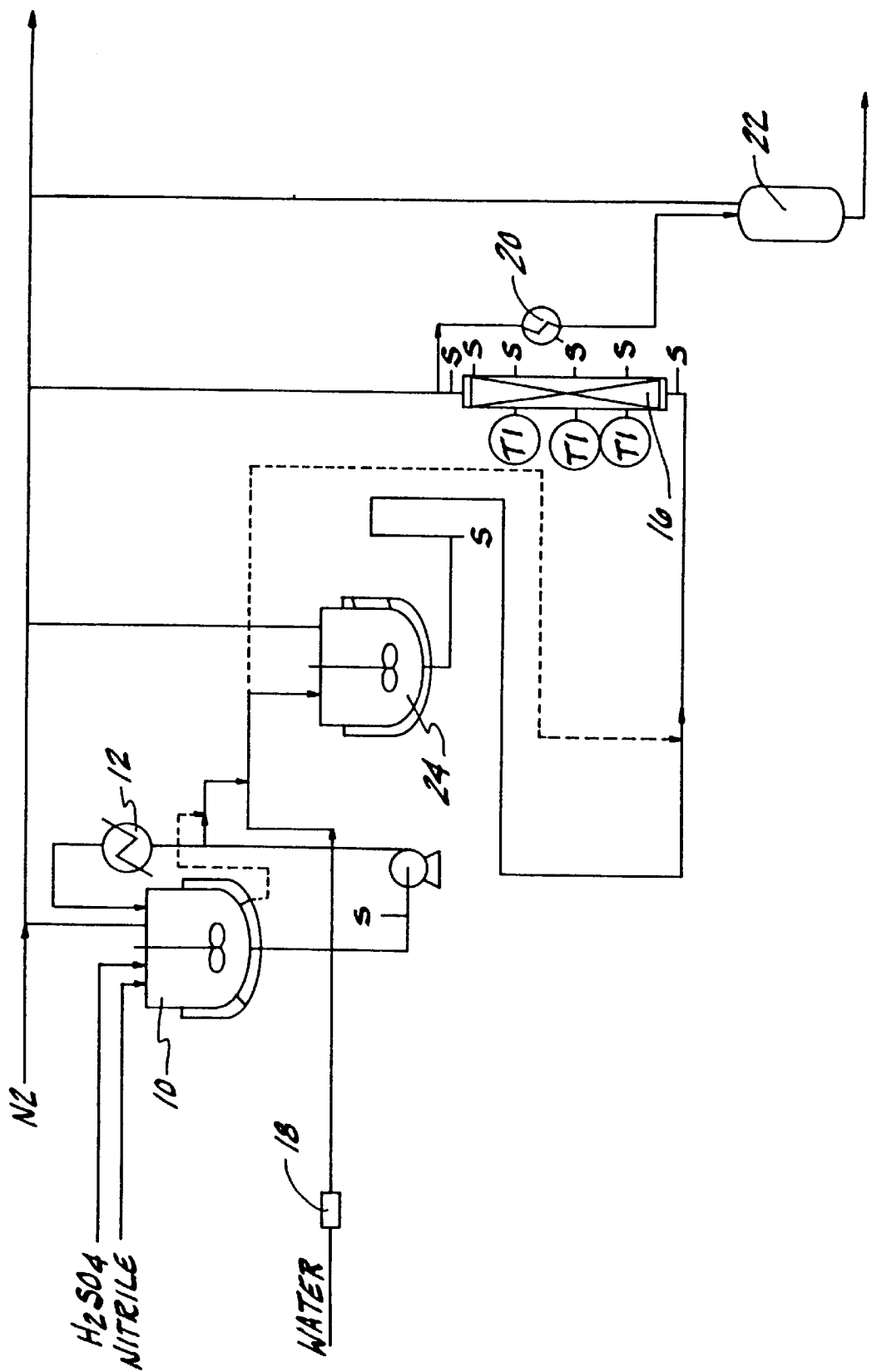
FIG. 2 is a schematic flowsheet of a process of the invention in which 2-hydroxy-4-methylthiobutanamide exiting a first reactor is converted to HMBA in a continuous stirred tank reactor and a plug flow reactor operated in series.

The hydrolyzate product leaving the PFR has a light color of between about 5 to about 10, preferably between about 5 to about 7, as measured using a Gardner calorimeter. Color is adversely affected by excessive PFR temperatures and residence time within the PFR. The PFR operates at a temperature between about 70° C. and about 120° C. When the PFR is operated adiabatically, the temperature rises along the flow path as the reaction product absorbs the adiabatic heat of reaction, reaching a point on the flow path (hot spot) at which the temperature reaches a plateau, and beyond which it may drop slightly if conditions are less than perfectly adiabatic. The peak temperature in the reactor is preferably between about 90° C. and about 120° C., more preferably between about 90° C. and about 105° C. The residence time of the finishing reaction solution within the PFR is between about 30 minutes and about 100 minutes, preferably between about 50 minutes and about 70 minutes. When the PFR is operated at a temperature above 110° C., a dark hydrolyzate may be produced. However, a PFR temperature below 90° C. may result in incomplete amide hydrolysis unless a high acid to nitrile molar ratio is employed. Darkening of the hydrolyzate product can also occur if the residence time exceeds about 120 minutes. A light colored hydrolyzate product is produced when an acid/nitrile molar ratio of between about 1.1 and about 1.5 is used during start up and normal operation when the PFR 16 is operated at a moderate temperature of between about 70 and about 95° C., preferably between about 80° C. and about 90° C. The PFR temperature can be reduced when it is operated adiabatically by lowering the temperature of the heated water stream entering the mixer 14. If the diluted aqueous hydrolysis solution is introduced into the preheater 23 (FIG. 1) before it is introduced to the PFR, the heat applied to the preheater can be reduced to lower the PFR operating temperature. Alternatively, cooling and/or heating may be provided to control the PFR temperature when the PFR is operated isothermally. When a second CSTR 24 precedes the PFR 16 as shown in FIG. 2, a darkened hydrolyzate product may be produced if the operating temperature of the second CSTR is too high. A light colored hydrolyzate product is produced when the above described acid/nitrile molar ratio is used and the second CSTR is operated at a moderate temperature of between about 70 and about 95° C., preferably between about 80° C. and about 90° C.

The PFRs best suited for use in the amide hydrolysis process of the invention are configured for operation at a Peclet number of at least 50 at a PFR operating temperature of at least 90° C. The Peclet number (Pe) is a measure of axial backmixing within the PFR as defined by the following equation:

$$Pe = uL/D$$

where: u=velocity, L=length, and D=axial dispersion coefficient. The Peclet number of a PFR is inversely proportional to axial back-mixing. Axial backmixing is effectively minimized when the Peclet number is at least 50, preferably between about 50 and about 200 or more, and residence time is between about 40 and about 100 minutes, preferably between about 50 and about 60 minutes.

The PFR 16 of the present invention may be pipeline PFR or a packed column PFR filled with a packing material. The amide hydrolysis reaction is non-zero order, but the kinetics of reaction have been found sufficiently favorable that high conversion may be realized within the relatively modest residence times noted above, and without substantial pressure drop. More particularly, it has been found that, where the nitrile has been substantially converted to amide, and the nitrile concentration is not greater than about 2% by weight in the stream entering the plug flow reactor, the residual amide and nitrile concentrations may each be reduced to not greater than about 0.2% by weight on an HMBA basis in a pipeline reactor that is operated with a velocity of the reacting solution in the turbulent flow range regime, for example, at a Reynolds number of at least about 3000, preferably at least about 5000. Provided that the nitrile/amide ratio of the solution entering the reactor is not greater than about 1% by weight in the stream entering the PFR, the amide and nitrile concentrations in the reaction product may each be reduced to not greater than about 0.1% by weight, HMBA basis. For the relatively modest residence time required to achieve such conversion, a PFR reactor operated may be operated at turbulent velocity without excessive pressure drop. Moreover, it has been found that the desired conversion may be attained at a modest operating temperature, in the range of between 90° C. and about 105° C., which does not require a high pressure reactor, and which allows the preparation of a product having a light color.

Alternatively, a packed column PFR may be used to carry out the final hydrolysis reaction. By use of structured packing, a packed column reactor may be operated at a significantly lower velocity than a pipeline reactor without significant backmixing due to wall effects or channeling. The packing promotes turbulence and radial mixing, and minimizes axial backmixing, dead spots and channelling of flow so that all fluid elements travel through the PFR in about the same residence time. Thus, a packed column reactor may have a substantially greater diameter and a more compact configuration than a pipeline reactor. It is particularly advantageous where reactants or products are of high viscosity.

However, for the process of the invention, it has been found that a pipeline reactor, i.e., an elongate tubular reactor substantially devoid of internal packing or other internal flow obstructions, is preferred. While a slightly greater degree of axial backmixing per unit length may be incurred in a pipeline reactor, the kinetics of the nitrile and amide hydrolysis have been discovered to allow nearly quantitative conversion with the modest residence times and low pressure drops described above. Because of low pressure drop incurred even at high velocity in a reactor suitable for the process of the invention, a pipeline reactor may be configured, i.e., with a high L/D (length to diameter) ratio, to operate at a very high Peclet number, typically in excess of 200, and readily in excess of 2000. Additionally, a pipeline reactor for the process of the invention can be constructed of relatively inexpensive materials of construction, e.g., teflon-lined carbon steel pipe. For a packed column reactor, more exotic materials of construction may be required. A pipeline reactor also affords greater flexibility since it can be operated at a much greater turndown ratio than a packed column, in the latter of which conversion declines sharply below a well defined threshold velocity. Threshold velocity in a packed column is attained in the transition between laminar and turbulent flow.

The PFR 16 is insulated to compensate for heat losses to the atmosphere. The heat of reaction generated during the amide hydrolysis is sufficient for autothermal operation under adiabatic conditions. Advantageously, the diluted aqueous hydrolysis solution can enter the PFR at a temperature below the reaction temperature for the amide hydrolysis. During autothermal operation, the heat of reaction generated by amide hydrolysis increases the temperature within the PFR, lessening the likelihood that a hot spot will form therein. The temperature profile in the PFR can be monitored through several temperature sensors T (FIGS. 1 and 2) along the length of the reactor. The hot water feed temperature can be adjusted to achieve the desired temperature profile in the PFR by increasing or decreasing the heat supplied to the water feed stream by the water heater 18 before it enters the mixer 14 to form the diluted aqueous hydrolysis solution. Additionally, the temperature of the diluted aqueous hydrolysis solution exiting the mixer 14 can be raised through the use of preheater 23 to increase the PFR operating temperature.

Although residual nitrile hydrolyzes in the inlet portion of the PFR, the nitrile hydrolysis should proceed sufficiently to completion in the CSTR 10 so that the exothermic reaction heat from the nitrile hydrolysis does not create a hot spot in the PFR that degrades hydrolyzate product quality and disrupts adiabatic autothermal operation of the PFR. Although hot spot temperatures of as much as 110° C. to about 120° C. can be tolerated within the PFR, the hydrolyzate product can darken significantly under such conditions.

The PFR operates at a total pressure of between about 0 and about 15 psig. A pressure control valve at the outlet of the PFR provides up to 15 psig back pressure to avoid boiling in the reactor system when the PFR operates at a temperature higher than 105° C.

Advantageously, hydrolysis solution samples may be withdrawn from sample valves S (FIGS. 1 and 2) and analyzed via gas chromatography to determine the hydrolysis solution composition profile along the length of the PFR. Once steady state conditions are established, a hydrolyzate sample can be removed from the PFR outlet every eight to twelve hours and quantitatively analyzed to monitor product quality.

The aqueous hydrolyzate product solution exiting the PFR 16 flows through a cooler 20 before being stored in a hydrolyzate product surge tank 22. The CSTRs, PFRs and the hydrolyzate product surge tank utilized in the processes of the present invention are operated under the same overhead pressure (preferably about 10 psig) by employing a common vent header which is blanketed with nitrogen and controlled by a pressure controller which relieves pressure by venting gases to an incinerator header when pressure exceeds about 15 psig. Venting may remove volatile organic sulfur compounds such as methyl sulfide, methyl disulfide, and methylmercaptan, which are by-products of the reaction. The vapor emissions are less than 0.5 scf per 1000 lbs. HMBA product, usually less than 0.3 scf per 1000 lbs. product. Emissions of 0.2 scf/1000 lbs. HMBA and even lower are readily achievable, especially where only a single CSTR is used.

The HMBA can be recovered from the aqueous hydrolyzate product solution by neutralization with ammonium hydroxide, or by extraction methods such as that described by Ruest et al. U.S. Pat. No. 4,524,077 which is incorporated herein by reference.

FIG. 2 illustrates an embodiment of the present invention wherein the amide hydrolysis is conducted in the PFR 16 and a second CSTR 24 upstream of the PFR. The second CSTR enables easy handling of the viscous amide, thoroughly mixes the hydrolysis solution, and controls the temperature and water content of the finishing reaction solution, resulting in a relatively low viscosity of the latter solution as introduced into the PFR. The nitrile hydrolysis takes place in CSTR 10 and the intermediate aqueous hydrolysis solution and a heated water feed stream are introduced into the second CSTR 24 wherein a substantial portion of the amide is hydrolyzed to HMBA. For purposes of the present invention, a substantial portion of the amide is hydrolyzed when more than 50% by weight, preferably between about 50% and about 80% by weight, of the amide is hydrolyzed to HMBA. The residence time during which the diluted aqueous hydrolysis solution is contained within the second CSTR 24 is between about 30 minutes and about 80 minutes, preferably between about 40 minutes and about 60 minutes. The liquid level in the second CSTR can be controlled by gravity overflow to the PFR 16 or by level control as previously described.

The amide hydrolysis reaction is initiated in the second CSTR at a temperature between about 70° C. and about 120° C., preferably between about 90° C. and about 105° C., and at a total pressure of between about 0 and about 15 psig. Conversion to HMBA is generally improved by operating the second CSTR at an elevated temperature between about 90° C. and about 110 ° C. The second CSTR 24 is provided with a steam heated jacket in order to maintain the operating temperature. If the temperature sensors T (FIG. 2) detect a hot spot within the PFR, the operating temperature of the second CSTR can be lowered.

The amide hydrolysis reaction is substantially carried out in the second CSTR, producing a finishing reaction solution which is introduced into the PFR 16. The finishing reaction solution comprises at least about 32 wt. % HMBA, at least about 25 wt. % ammonium bisulfate, at least about 25 wt. % water, up to about 5 wt. % amide and up to about 1 wt. % nitrile. Preferably, the finishing reaction solution comprises between about 31 and about 42 wt. % HMBA, between about 20 and about 30 wt. % ammonium bisulfate, between about 20 and about 30 wt. % water, between about 2 and about 5 wt. % amide and up to about 1 wt. % nitrile. The amide hydrolysis is then completed within the PFR as described above for FIG. 1.

Figure 3:
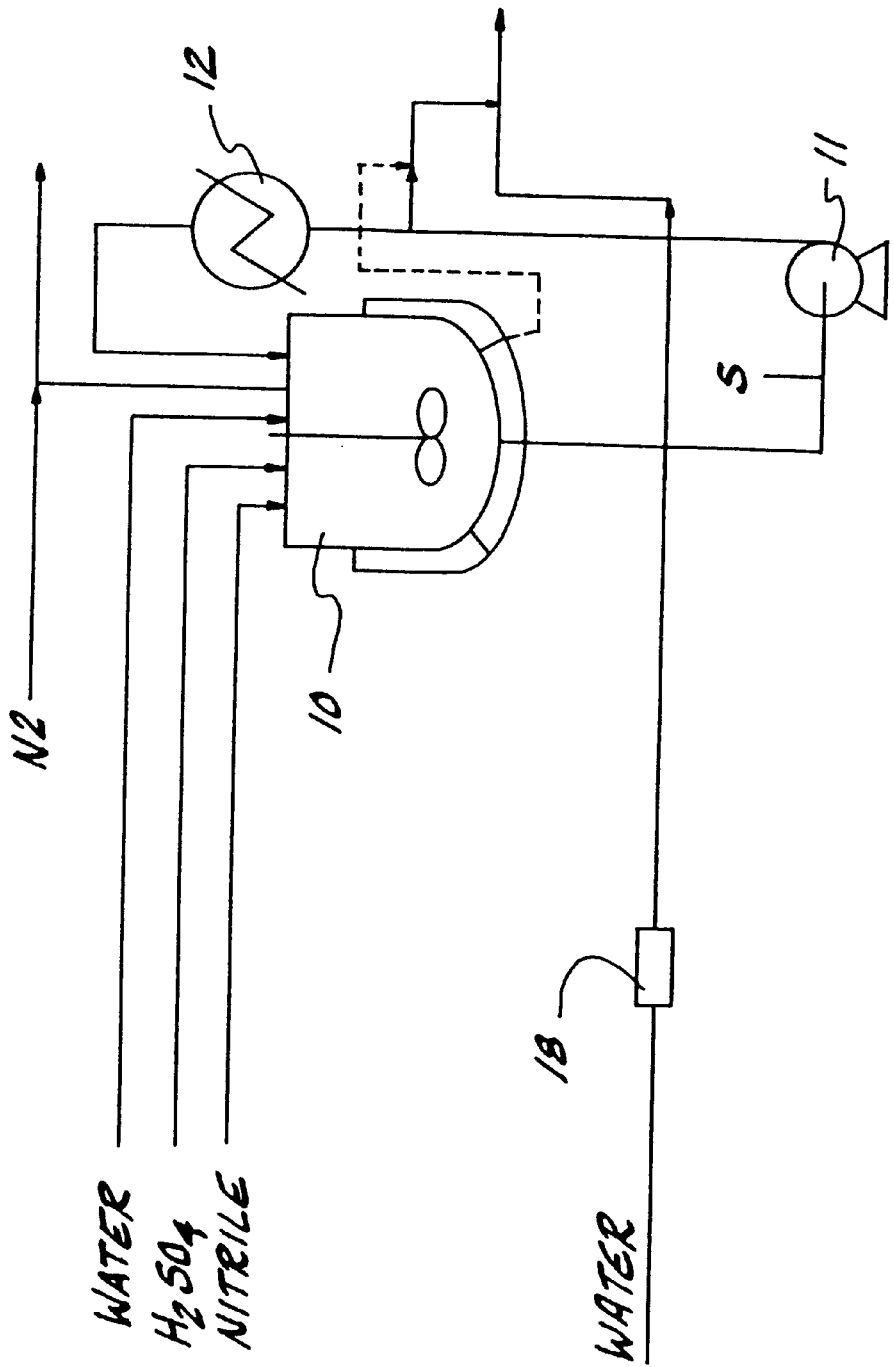
FIG. 3 is a schematic illustration of a continuous stirred tank reactor adapted for conversion of HMBN to 2-hydroxy-4-methylthiobutanamide while a concentrated sulfuric acid stream is introduced into the reactor.

FIG. 3 illustrates a preferred embodiment of the invention wherein the CSTR 10 can be adapted in the processes shown in FIGS. 1 and 2 to receive concentrated sulfuric acid, HMBN, and water feed streams. When the streams are simultaneously fed to the reactor, sulfuric acid is diluted in the reactor as the nitrile hydrolysis reaction occurs. A separate acid dilution system is not required and associated installation and maintenance costs are avoided. The concentrated sulfuric acid introduced into the CSTR 10 has a strength of between about 70% by weight and about 99% by weight, preferably between about 90% by weight and about 98% by weight. The aqueous hydrolysis solution within the CSTR 10 has a strength of between about 50% by weight and about 70% by weight, preferably between about 60% by weight and about 70% by weight of sulfuric acid on an organic-free basis. The aqueous hydrolysis solution is continuously pumped through an external heat exchanger 12 at a high circulation rate to remove heat of reaction. A pump 11 circulates reacting solution between CSTR 10 and an external heat exchanger 12, in which exothermic heat of reaction is removed by transfer to a coolant. The heat exchanger also removes the heat generated by dilution of sulfuric acid when concentrated sulfuric acid is fed directly to reactor 10.

The process of the present invention provides an improved method for preparing HMBA. High productivity can be achieved using such a process because it can be operated continuously to provide greater throughput than a conventional batch process. The process significantly reduces capital and maintenance costs associated with batch processes, for example, by eliminating the need for separate sulfuric acid dilution when concentrated sulfuric acid is introduced to a reactor without prior dilution. The process also affords improved control of reaction conditions as compared to conventional batch hydrolysis systems. Such improved control of the hydrolysis reactions enables production of a hydrolyzate solution of consistently high quality. The process vent emissions are significantly reduced as compared to conventional batch systems because filling and emptying of tanks and operation at non-steady state conditions is eliminated.

The following examples are presented to describe preferred embodiments and utilities of the present invention and are not meant to limit the present invention unless otherwise stated in the claims appended hereto.

EXAMPLE 1

Figure 4:
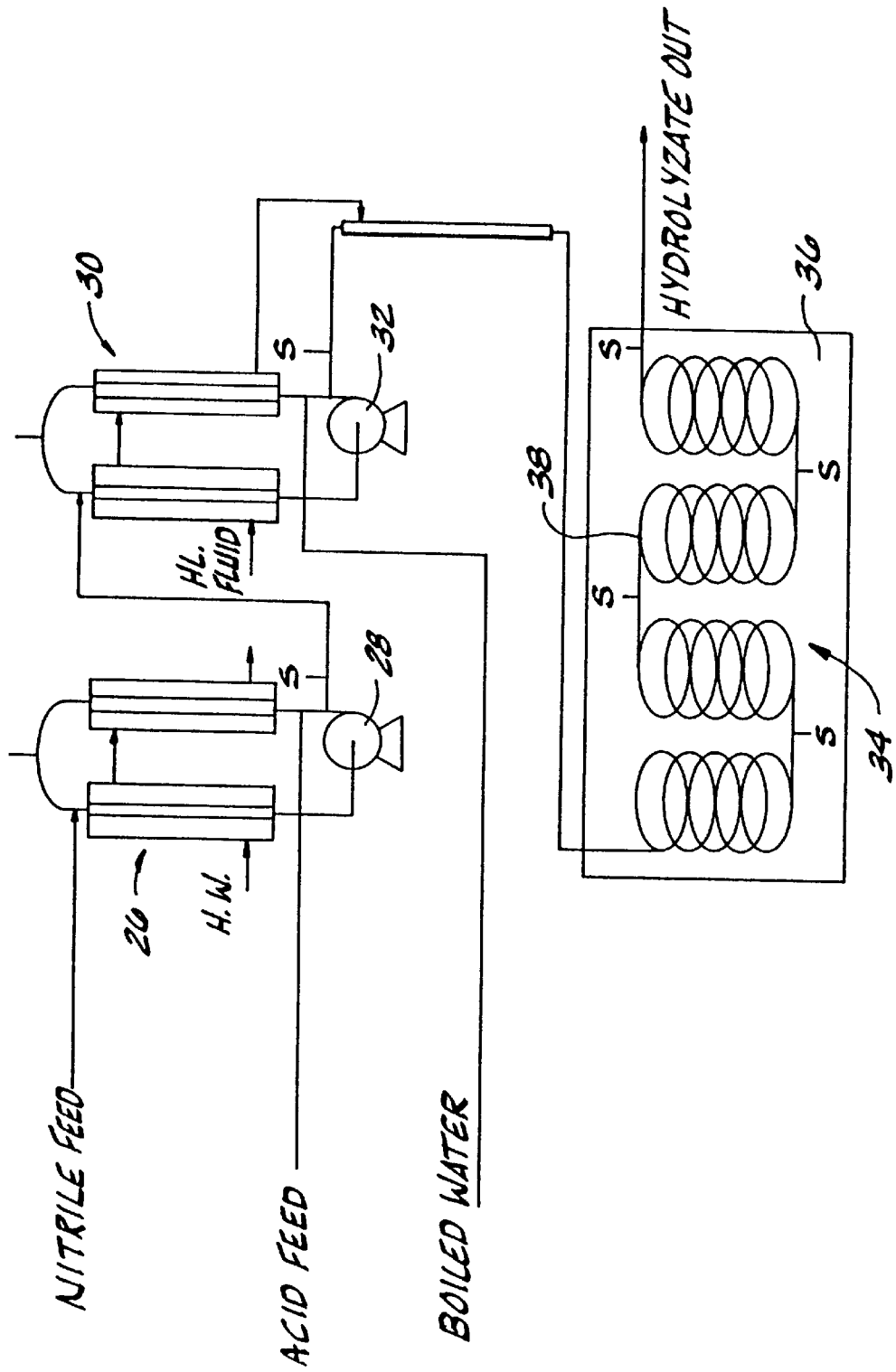
FIG. 4 is a schematic flowsheet of a bench-scale continuous hydrolysis process in which 2-hydroxy-4-methylthiobutanamide exiting a first recirculating reactor is converted to HMBA in a second recirculating reactor and a plug flow reactor operated in series.

Bench scale equipment as shown in FIG. 4 was used to demonstrate the continuous hydrolysis process.

Nitrile (2-hydroxy-4-methylthiobutanenitrile) and 65% aqueous sulfuric acid were continuously pumped at rates of 1.01 g/min and 1.167 g/min, respectively, into a well-mixed recirculating reactor 26 having a liquid volume of 42.1 milliliters. The reaction temperature was controlled at 65° C. through cooling jackets provided on the recirculating reactor loop, which removed the heat released from the nitrile hydrolysis reaction. A pump 28 recirculated the aqueous hydrolysis solution in the reactor loop. The residence time of the reactor 26 based on the total feed rate was 25.4 minutes. At the outlet of the reactor, a sample was periodically removed during steady state conditions. All sampling ports are designated with an S in FIG. 4. The sample was analyzed by a gas chromatographic method to determine the hydrolyzate product composition leaving the reactor. The gas chromatography result showed that practically all nitrile feed was hydrolyzed and converted to amide and approximately 15% of the formed amide was further hydrolyzed in this reactor to form HMBA, the final hydrolysis product.

The amide rich hydrolyzate leaving the recirculating reactor 26 was fed continuously into the second recirculating reactor 30 which is similar to the first recirculating reactor 26 but has a liquid volume of 119.3 milliliters. A water feed at 0.57 g/min was also introduced into the second well-mixed reactor which provided a residence time of 52.6 minutes. The temperature of this reactor loop was maintained at 102° C. via a heating fluid jacket provided on the recirculating reactor loop. A pump 32 recirculated the hydrolyzate in the reactor loop. An outlet sample from the reactor 30 was obtained and analyzed by gas chromatography which revealed that approximately 94.5% of the feed amide was hydrolyzed to HMBA.

The outlet from the second recirculating reactor 30 continuously entered the final finishing reactor which was constructed of a series of four coils 34 of Teflon tubing. The finishing reactor was placed inside a constant temperature oven 36 for preventing heat losses to the ambient, thus maintaining a temperature of 102° C. throughout the reactor coils 34. This isothermal PFR having a total liquid volume of 91 milliliters and a corresponding 43 minutes residence time was designed to assure completion of the amide hydrolysis. In this case, the hydrolysis of amide was completed at the outlet of the third coil 38. The hydrolyzate product taken from the outlet of the PFR was analyzed and contained 35% HMBA, with the remaining material being water and by-product ammonium bisulfate. The color of the hydrolyzate product was 6–7 on the Gardner color scale.

EXAMPLES 2–9

The same continuous bench scale equipment as used in Example 1 was also used to determine the effect of residence time and reaction temperature on conversion. The acid to nitrile feed ratio of each example was maintained at approximately a 1.0 molar stoichiometric ratio. At the outlet of each recirculating reactor and the end of each coil of the PFR, a sample (indicated as RECIRC and S, respectively, in Tables 1–8 below) was removed during steady state conditions and was analyzed by a gas chromatographic method to determine the hydrolysis solution composition leaving the reactor or coil. The hydrolysis solution composition and the temperature and residence time in each reactor or coil are shown in Tables 1–8 below. The remainder of the product included water and ammonium bisulfate. The results, based on various feed rates (1.01–2.33 grams/min. nitrile feed) and temperatures (60–65° C. for nitrile hydrolysis and 90–120° C. for amide hydrolysis) illustrate that increasing residence time and reaction temperatures improves the conversion of both hydrolysis reactions. However, increasing temperatures also resulted in an increase in product color.

EXAMPLE 2

Nitrile at 1.01 g/min was fed to the first recirculating reactor, along with 1.15 g/min 64.7% sulfuric acid, giving a 0.99 acid/nitrile molar ratio. A water feed at 0.55 g/min was also introduced into the second recirculating reactor. The hydrolysis solution composition and the temperature and residence time in each reactor or coil are shown in Table 1 below.

TABLE 1

|  | RECIRC-I | RECIRC-II | S1 | S2 | S3 |
|---|---|---|---|---|---|
| Temperature (° C.) | 64 | 103 | 104 | 104 | 104 |
| Residence Time (min) | 25 | 53 | 11 | 11 | 11 |
| Hydrolysis Solution Composition (wt. %) | | | | | |
| Nitrile | 0.11 | trace | trace | trace | trace |
| HMBA | 8.3 | 34 | 33 | 35 | 33 |
| Amide | 38 | 2.7 | 0.70 | 0.12 | 0.03 |

Hydrolyzate Product Color: 6–7 on Gardner scale

EXAMPLE 3

Nitrile at 1.01 g/min was fed to the first recirculating reactor, along with 1.16 g/min 64.7% sulfuric acid, giving a 0.99 acid/nitrile molar ratio. A water feed at 0.54 g/min was also introduced into the second recirculating reactor. The hydrolysis solution composition and the temperature and residence time in each reactor or coil are shown in Table 2 below.

TABLE 2

|  | RECIRC-I | RECIRC-II | S1 | S2 | S3 |
|---|---|---|---|---|---|
| Temperature (° C.) | 62 | 98 | 102 | 102 | 102 |
| Residence Time (min) | 25 | 53 | 11 | 11 | 11 |
| Hydrolysis Solution Composition (wt. %) | | | | | |
| Nitrile | 0.22 | 0.05 | 0.05 | trace | 0.035 |
| HMBA | 7.8 | 33 | 38 | 38 | 39 |
| Amide | 35 | 3.5 | 0.81 | 0.18 | 0.09 |

Hydrolyzate Product Color: 5–6 on Gardner scale

EXAMPLE 4

Nitrile at 1.43 g/min was fed to the first recirculating reactor, along with 1.65 g/min 64.7% sulfuric acid, giving a 0.99 acid/nitrile molar ratio. A water feed at 0.76 g/min was also introduced into the second recirculating reactor. The hydrolysis solution composition and the temperature and residence time in each reactor or coil are shown in Table 3 below.

TABLE 3

|  | RECIRC-I | RECIRC-II | S1 | S2 | S3 |
|---|---|---|---|---|---|
| Temperature (° C.) | 65 | 105 | 105 | 105 | 105 |
| Residence Time (min) | 18 | 36 | 7.7 | 7.7 | 7.7 |
| Hydrolysis Solution Composition (wt. %) | | | | | |
| Nitrile | 0.36 | 0.06 | 0.05 | trace | trace |
| HMBA | 6.7 | 34 | 36 | 37 | 38 |
| Amide | 39 | 3.1 | 0.79 | 0.28 | trace |

Hydrolyzate Product Color: 6–7 on Gardner scale

EXAMPLE 5

Nitrile at 1.45 g/min was fed to the first recirculating reactor, along with 1.69 g/min 64.7% sulfuric acid, giving a 1.0 acid/nitrile molar ratio. A water feed at 0.78 g/min was also introduced into the second recirculating reactor. The hydrolysis solution composition and the temperature and residence time in each reactor or coil are shown in Table 4 below.

TABLE 4

|  | RECIRC-I | RECIRC-II | S1 | S2 | S3 | S4 |
|---|---|---|---|---|---|---|
| Temperature (° C.) | 65 | 90 | 90 | 90 | 90 | 90 |
| Residence Time (min) | 18 | 37 | 7.7 | 7.7 | 7.7 | 7.3 |
| Hydrolysis Solution Composition (wt. %) | | | | | | |
| Nitrile | 0.37 | trace | trace | trace | trace | trace |
| HMBA | 6.1 | 32 | 36 | 37 | 36 | 37 |
| Amide | 40 | 5.8 | 2.1 | 0.99 | 0.60 | 0.40 |

Hydrolyzate Product Color: 4 on Gardner scale

EXAMPLE 6

Nitrile at 2.0 g/min was fed to the first recirculating reactor, along with 2.33 g/min 65% sulfuric acid, giving a 1.01 acid/nitrile molar ratio. A water feed at 1.09 g/min was also introduced into the second recirculating reactor. The hydrolysis solution composition and the temperature and residence time in each reactor or coil are shown in Table 5 below.

TABLE 5

|  | RECIRC-I | RECIRC-II | S1 | S2 | S3 | S4 |
|---|---|---|---|---|---|---|
| Temperature (° C.) | 65 | 105 | 105 | 105 | 105 | 105 |
| Residence Time (min) | 13 | 26 | 5.4 | 5.4 | 5.4 | 5.2 |

TABLE 5-continued

|   | RECIRC-I | RECIRC-II | S1 | S2 | S3 | S4 |
|---|---|---|---|---|---|---|
| Hydrolysis Solution Composition (wt. %) | | | | | | |
| Nitrile | 0.45 | 0.09 | trace | 0.04 | trace | 0.06 |
| HMBA | 5.3 | 34 | 36 | 36 | 36 | 37 |
| Amide | 40 | 3.3 | 0.84 | 0.28 | 0.12 | 0.07 |

Hydrolyzate Product Color: 6–7 on Gardner scale

EXAMPLE 7

Nitrile at 1.42 g/min was fed to the first recirculating reactor, along with 1.65 g/min 65% sulfuric acid, giving a 1.01 acid/nitrile molar ratio. A water feed at 0.795 g/min was also introduced into the second recirculating reactor. The hydrolysis solution composition and the temperature and residence time in each reactor or coil are shown in Table 6 below.

TABLE 6

|   | RECIRC-I | RECIRC-II | S1 | S2 | S3 |
|---|---|---|---|---|---|
| Temperature (° C.) | 60 | 120 | 120 | 120 | 120 |
| Residence Time (min) | 18 | 36 | 7.5 | 7.5 | 7.5 |
| Hydrolysis Solution Composition (wt. %) | | | | | |
| Nitrile | 0.23 | 0.05 | trace | trace | trace |
| HMBA | 5.2 | 36 | 35 | 36 | 36 |
| Amide | 39 | 1.5 | trace | trace | trace |

Hydrolyzate Product Color: 17 on Gardner scale

EXAMPLE 8

Nitrile at 1.43 g/min was fed to the first recirculating reactor, along with 1.66 g/min 65% sulfuric acid, giving a 1.0 acid/nitrile molar ratio. A water feed at 0.78 g/min was also introduced into the second recirculating reactor. The hydrolysis solution composition and the temperature and residence time in each reactor or coil are shown in Table 7 below.

TABLE 7

|   | RECIRC-I | RECIRC-II | S1 | S2 | S4 |
|---|---|---|---|---|---|
| Temperature (° C.) | 65 | 100 | 100 | 100 | 100 |
| Residence Time (min) | 18 | 36 | 7.6 | 7.6 | 7.3 |

TABLE 7-continued

|   | RECIRC-I | RECIRC-II | S1 | S2 | S4 |
|---|---|---|---|---|---|
| Hydrolysis Solution Composition (wt. %) | | | | | |
| Nitrile | 0.26 | 0.10 | NA | NA | trace |
| HMBA | 7.0 | 34 | NA | NA | 37 |
| Amide | 36 | 3.7 | NA | NA | 0.05 |

Hydrolyzate Product Color: 6 on Gardner scale

EXAMPLE 9

Nitrile at 1.04 g/min was fed to the first recirculating reactor, along with 1.15 g/min 65% sulfuric acid, giving a 0.96 acid/nitrile molar ratio. A water feed at 0.57 g/min was also introduced into the second recirculating reactor. The hydrolysis solution composition and the temperature and residence time in each reactor or coil are shown in Table 8 below.

TABLE 8

|   | RECIRC-I | RECIRC-II | S1 | S2 | S3 | S4 |
|---|---|---|---|---|---|---|
| Temperature (° C.) | 65 | 100 | 100 | 100 | 100 | 100 |
| Residence Time (min) | 25 | 52 | 11 | 11 | 11 | 11 |
| Hydrolysis Solution Composition (wt. %) | | | | | | |
| Nitrile | 0.36 | 0.08 | 0.05 | 0.05 | 0.04 | trace |
| HMBA | 8.7 | 35 | 37 | 36 | 35 | 34 |
| Amide | 39 | 3.6 | 0.89 | 0.37 | 0.17 | 0.05 |

Hydrolyzate Product Color: 6 on Gardner scale

EXAMPLES 10–20

Figure 5:
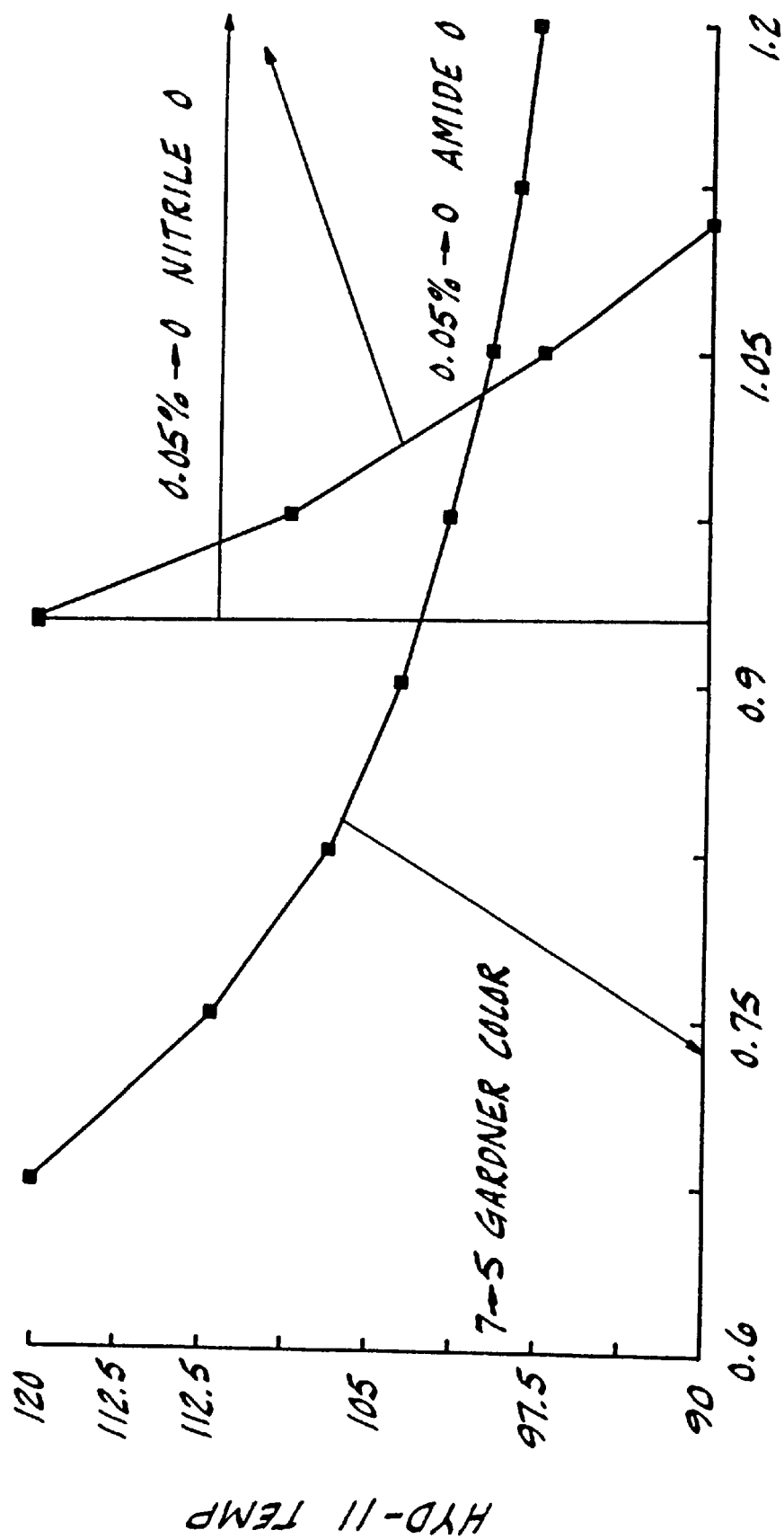
FIG. 5 is a plot showing amide concentration, nitrile concentration, and Gardner color for the hydrolyzate product as a function of acid/nitrile molar ratio fed to the first reactor and temperature within the plug flow reactor based on bench scale experiments.

The effect of acid/nitrile feed molar ratio on the reaction conversion, as well as the coupling effect of this ratio with reaction temperature was determined. In these examples, the nitrile feed rate was essentially constant and the water feed rate was adjusted for various 65% sulfuric acid feeds to assure the same water content of the final hydrolyzate from each run. At the outlet of each reactor and the end of each coil of the PFR, a sample was removed during steady state conditions and was analyzed by a gas chromatographic method to determine the hydrolyzate product composition leaving the reactor or coil. The hydrolysis solution composition and the temperature and residence time in each reactor or coil are shown below. The remainder of the hydrolyzate included water and ammonium bisulfate. Based on the range of the variables that were analyzed, i.e., acid/nitrile molar ratio from 0.6 to 1.2 and amide hydrolysis temperature from 90–120° C., an optimum range of conditions were derived as shown in FIG. 5 for the fixed residence (or nitrile feed rate) tested. Within the range of 90–101° C. and 1.0–1.2 acid/nitrile ratio, any combination of temperature and acid/nitrile molar ratio will result in a satisfactory product containing up to 0.05% by weight amide, up to 0.05% by weight nitrile and having a color of between 5 and 7 on a Gardner scale.

EXAMPLE 10

Nitrile at 1.02 g/min was fed to the first recirculating reactor, along with 1.03 g/min 64.75% sulfuric acid, giving a 0.88 acid/nitrile molar ratio. A water feed at 0.53 g/min was also introduced into the second recirculating reactor. The hydrolysis solution composition and the temperature and residence time in each reactor or coil are shown in Table 9 below.

TABLE 9

|  | RECIRC-I | RECIRC-II | S1 | S2 | S3/S4 |
|---|---|---|---|---|---|
| Temperature (° C.) | 65 | 105 | 105 | 105 | 105 |
| Residence Time (min) | 27 | 53 | 11 | 11 | 11 |
| Hydrolysis Solution Composition (wt. %) | | | | | |
| Nitrile | 0.80 | 0.31 | 0.35 | 0.40 | NA |
| HMBA | 8.3 | 35 | 41 | 49 | NA |
| Amide | 41 | 3.7 | 1.7 | 0.96 | NA |

Hydrolyzate Product Color: 6–7 on Gardner scale

EXAMPLE 11

Nitrile at 0.99 g/min was fed to the first recirculating reactor, along with 0.70 g/min 65% sulfuric acid, giving a 0.62 acid/nitrile molar ratio. A water feed at 0.94 g/min was also introduced into the second recirculating reactor. The hydrolysis solution composition and the temperature and residence time in each reactor or coil are shown in Table 10 below.

TABLE 10

|  | RECIRC-I | RECIRC-II | S1 | S2 | S3 | S4 |
|---|---|---|---|---|---|---|
| Temperature (° C.) | 65 | 90 | 90 | 90 | 90 | 90 |
| Residence Time (min) | 32 | 53 | 11 | 11 | 11 | 11 |
| Hydrolysis Solution Composition (wt. %) | | | | | | |
| Nitrile | 5.2 | 2.2 | 2.4 | 2.5 | 2.5 | 2.5 |
| HMBA | 7.9 | 25 | 27 | 29 | 30 | 30 |
| Amide | 45 | 9.5 | 7.4 | 5.9 | 5.2 | 4.6 |

Hydrolyzate Product Color: 5 on Gardner scale

EXAMPLE 12

Nitrile at 1.01 g/min was fed to the first recirculating reactor, along with 1.37 g/min 64.75% sulfuric acid, giving a 1.19 acid/nitrile molar ratio. A water feed at 0.53 g/min was also introduced into the second recirculating reactor. The hydrolysis solution composition and the temperature and residence time in each reactor or coil are shown in Table 11 below.

TABLE 11

|  | RECIRC-I | RECIRC-II | S1 | S2 | S3 | S4 |
|---|---|---|---|---|---|---|
| Temperature (° C.) | 65 | 90 | 90 | 90 | 90 | 90 |
| Residence Time (min) | 23 | 50 | 10 | 10 | 10 | 10 |
| Hydrolysis Solution Composition (wt. %) | | | | | | |
| Nitrile | trace | trace | trace | trace | trace | trace |
| HMBA | 7.7 | 31 | 35 | 34 | 35 | 35 |
| Amide | 33 | 2.8 | 0.72 | 0.17 | 0.03 | trace |

Hydrolyzate Product Color: 5 on Gardner scale

EXAMPLE 13

Nitrile at 1.01 g/min was fed to the first recirculating reactor, along with 0.70 g/min 65% sulfuric acid, giving a 0.60 acid/nitrile molar ratio. A water feed at 0.90 g/min was also introduced into the second recirculating reactor. The hydrolysis solution composition and the temperature and residence time in each reactor or coil are shown in Table 12 below.

TABLE 12

|  | RECIRC-I | RECIRC-II | S1 | S2 | S3 | S4 |
|---|---|---|---|---|---|---|
| Temperature (° C.) | 65 | 120 | 120 | 120 | 120 | 120 |
| Residence Time (min) | 32 | 52 | 11 | 11 | 11 | 10 |
| Hydrolysis Solution Composition (wt. %) | | | | | | |
| Nitrile | 6.0 | 2.6 | 2.7 | 2.2 | 2.7 | 2.3 |
| HMBA | 7.7 | 27 | 32 | 29 | 34 | 31 |
| Amide | 44 | 5.4 | 4.0 | 1.4 | 1.8 | 1.4 |

Hydrolyzate Product Color: 10 on Gardner scale

EXAMPLE 14

Nitrile at 1.0 g/min was fed to the first recirculating reactor, along with 1.37 g/min 64.75% sulfuric acid, giving a 1.19 acid/nitrile molar ratio. A water feed at 0.513 g/min was also introduced into the second recirculating reactor. The hydrolysis solution composition and the temperature and residence time in each reactor or coil are shown in Table 13 below.

TABLE 13

|  | RECIRC-I | RECIRC-II | S1 | S2 | S3 | S4 |
|---|---|---|---|---|---|---|
| Temperature (° C.) | 65 | 120 | 120 | 120 | 120 | 120 |
| Residence Time (min) | 23 | 50 | 10 | 10 | 10 | 10 |
| Hydrolysis Solution Composition (wt. %) | | | | | | |
| Nitrile | trace | trace | trace | trace | trace | trace |
| HMBA | 8.5 | 34 | 34 | 35 | 35 | 34 |
| Amide | 31 | 0.44 | trace | trace | trace | trace |

Hydrolyzate Product Color: 12+ on Gardner scale

EXAMPLE 15

Nitrile at 1.0 g/min was fed to the first recirculating reactor, along with 1.05 g/min 64.75% sulfuric acid, giving a 0.91 acid/nitrile molar ratio. A water feed at 0.67 g/min was also introduced into the second recirculating reactor. The hydrolysis solution composition and the temperature and residence time in each reactor or coil are shown in Table 14 below.

TABLE 14

|  | RECIRC-I | RECIRC-II | S1 | S2 | S3 | S4 |
|---|---|---|---|---|---|---|
| Temperature (° C.) | 65 | 105 | 105 | 105 | 105 | 105 |
| Residence Time (min) | 27 | 53 | 11 | 11 | 11 | 11 |
| Hydrolysis Solution Composition (wt. %) | | | | | | |
| Nitrile | 0.39 | 0.11 | 0.11 | 0.11 | 0.10 | 0.09 |
| HMBA | 8.9 | 34 | 34 | 37 | 38 | 38 |
| Amide | 37 | 4.0 | 1.5 | 0.71 | 0.32 | 0.20 |

Hydrolyzate Product Color: 6 on Gardner scale

EXAMPLE 16

Nitrile at 1.02 g/min was fed to the first recirculating reactor, along with 0.71 g/min 64.75% sulfuric acid, giving a 0.6 acid/nitrile molar ratio. A water feed at 0.93 g/min was also introduced into the second recirculating reactor. The hydrolysis solution composition and the temperature and residence time in each reactor or coil are shown in Table 15 below.

TABLE 15

|  | RECIRC-I | RECIRC-II | S1 | S2 | S3 | S4 |
|---|---|---|---|---|---|---|
| Temperature (° C.) | 65 | 120 | 120 | 120 | 120 | 120 |
| Residence Time (min) | 32 | 52 | 11 | 11 | 11 | 10 |
| Hydrolysis Solution Composition (wt. %) | | | | | | |
| Nitrile | 5.7 | 2.5 | 2.7 | 2.6 | 2.6 | 2.5 |
| HMBA | 8.5 | 29 | 33 | 34 | 35 | 35 |
| Amide | 45 | 6.2 | 4.3 | 2.6 | 2.0 | 1.5 |

Hydrolyzate Product Color: 6 on Gardner scale

EXAMPLE 17

Nitrile at 1.02 g/min was fed to the first recirculating reactor, along with 0.69 g/min 65% sulfuric acid, giving a 0.59 acid/nitrile molar ratio. A water feed at 0.90 g/min was also introduced into the second recirculating reactor. The hydrolysis solution composition and the temperature and residence time in each reactor or coil are shown in Table 16 below.

TABLE 16

|  | RECIRC-I | RECIRC-II | S1 | S2 | S3 | S4 |
|---|---|---|---|---|---|---|
| Temperature (° C.) | 65 | 90 | 90 | 90 | 90 | 90 |
| Residence Time (min) | 32 | 53 | 11 | 11 | 11 | 10 |
| Hydrolysis Solution Composition (wt. %) | | | | | | |
| Nitrile | 6.0 | 3.4 | 3.2 | 3.2 | 3.3 | 3.3 |
| HMBA | 8.2 | 25 | 27 | 28 | 29 | 30 |
| Amide | 44 | 12 | 8.0 | 7.5 | 6.6 | 5.7 |

Hydrolyzate Product Color: 5 on Gardner scale

EXAMPLE 18

Nitrile at 1.02 g/min was fed to the first recirculating reactor, along with 1.38 g/min 65% sulfuric acid, giving a 1.18 acid/nitrile molar ratio. A water feed at 0.54 g/min was also introduced into the second recirculating reactor. The hydrolysis solution composition and the temperature and residence time in each reactor or coil are shown in Table 17 below.

TABLE 17

|  | RECIRC-I | RECIRC-II | S1 | S2 | S3 | S4 |
|---|---|---|---|---|---|---|
| Temperature (° C.) | 65 | 90 | 90 | 90 | 90 | 90 |
| Residence Time (min) | 23 | 50 | 10 | 10 | 10 | 10 |
| Hydrolysis Solution Composition (wt. %) | | | | | | |
| Nitrile | trace | trace | trace | trace | trace | trace |
| HMBA | 7.2 | 31 | 35 | 35 | 35 | 36 |
| Amide | 34 | 2.9 | 0.75 | 0.24 | trace | trace |

Hydrolyzate Product Color: 5 on Gardner scale

EXAMPLE 19

Nitrile at 1.03 g/min was fed to the first recirculating reactor, along with 1.39 g/min 65% sulfuric acid, giving a 1.17 acid/nitrile molar ratio. A water feed at 0.52 g/min was also introduced into the second recirculating reactor. The hydrolysis solution composition and the temperature and residence time in each reactor or coil are shown in Table 18 below.

TABLE 18

|  | RECIRC-I | RECIRC-II | S1 | S2 | S3 | S4 |
|---|---|---|---|---|---|---|
| Temperature (° C.) | 65 | 120 | 120 | 120 | 120 | 120 |
| Residence Time (min) | 23 | 50 | 10 | 10 | 10 | 10 |
| Hydrolysis Solution Composition (wt. %) | | | | | | |
| Nitrile | trace | trace | trace | trace | trace | trace |
| HMBA | 7.1 | 33 | 33 | 34 | 34 | 48 |
| Amide | 35 | 0.39 | trace | trace | trace | trace |

Hydrolyzate Product Color: >18 on Gardner scale

EXAMPLE 20

Nitrile at 1.02 g/min was fed to the first recirculating reactor, along with 1.05 g/min 65% sulfuric acid, giving a 0.90 acid/nitrile molar ratio. A water feed at 0.63 g/min was also introduced into the second recirculating reactor. The hydrolysis solution composition and the temperature and residence time in each reactor or coil are shown in Table 19 below.

TABLE 19

|  | RECIRC-I | RECIRC-II | S1 | S2 | S3 | S4 |
|---|---|---|---|---|---|---|
| Temperature (° C.) | 65 | 105 | 105 | 105 | 105 | 105 |
| Residence Time (min) | 27 | 53 | 11 | 11 | 11 | 11 |
| Hydrolysis Solution Composition (wt. %) | | | | | | |
| Nitrile | 0.38 | 0.06 | 0.09 | 0.06 | 0.09 | 0.09 |
| HMBA | 8.9 | 28 | 39 | 31 | 41 | 38 |
| Amide | 40 | 2.5 | 0.97 | 0.31 | 0.18 | 0.10 |

Hydrolyzate Product Color: 7 on Gardner scale

EXAMPLE 21

Figure 6:
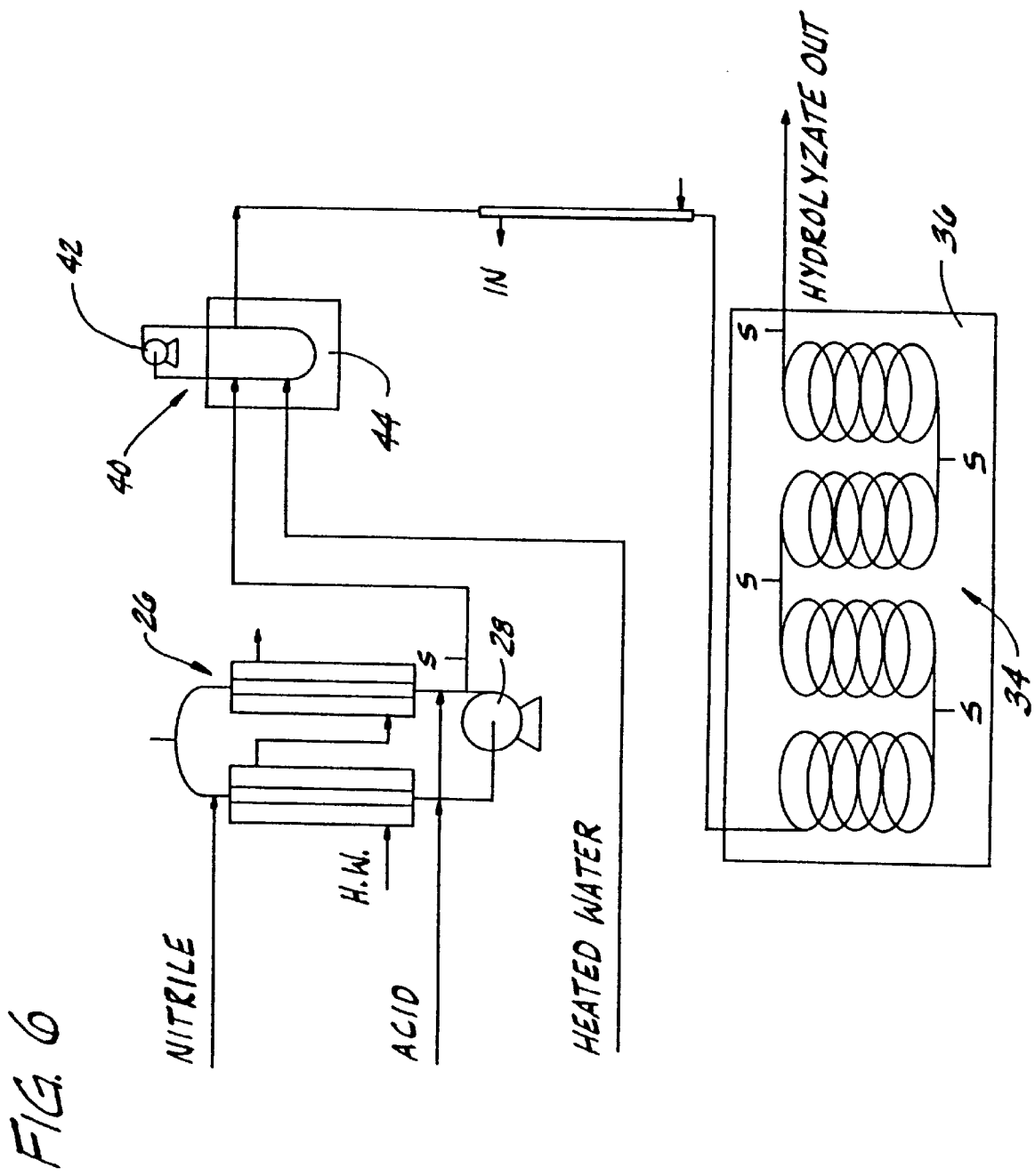
FIG. 6 is a schematic flowsheet of a bench-scale continuous hydrolysis process in which 2-hydroxy-4-methylthiobutanamide exiting a first reactor is introduced into a plug flow reactor and hydrolyzed to produce HMBA.

The bench scale equipment used in the preceding examples was modified by replacing the second recirculating reactor 30 with a small mixing loop 40 with negligible volume used for mixing the water feed and the hydrolysis solution leaving the first loop reactor 26. The diluted aqueous hydrolysis solution was recirculated through the mixing loop by a pump 42. The mixer loop 40 was heated in a hot water bath 44 in order to heat the diluted aqueous hydrolysis solution before it entered the PFR in which the amide hydrolysis reaction occurred. The modified bench scale equipment is shown in FIG. 6.

Nitrile at 0.73 g/min was fed to the first recirculating reactor, along with 0.83 g/min 65% sulfuric acid, giving a 0.99 acid/nitrile molar ratio. The temperature in the reactor loop was 60° C. and the residence time was estimated as 36.8 minutes. Analysis of the reactor outlet sample revealed that nitrile was essentially hydrolyzed to amide with less than 0.1% unreacted nitrile remaining in the outlet stream. The temperature of the hydrolysis solution at the outlet of the mixer loop was 75° C. and the residence time in the mixer loop was 1.5 minutes. The PFR coils were maintained at 100 to 101° C. The residence time in each of the first three coils was 16 minutes and that in the last coil was 15.2 minutes. Amide hydrolysis was completed in the last PFR coil.

EXAMPLE 22

The equipment used in the continuous hydrolysis process as shown in FIG. 2 consists of two CSTRs and one packed column type PFR. The first CSTR was devoted for the nitrile hydrolysis while the second CSTR and PFR were for the amide hydrolysis. The PFR is an 8 inch diameter teflon lined carbon steel pipe packed with Koch SMVP Teflon packing. The PFR was manufactured by Koch Engineering. The threshold velocity for the SMVP packing is 0.95 mm/sec.

105 lbs/hr of nitrile and 121 lbs/hr of 65% sulfuric acid were continuously fed to the first 20 gallon CSTR in which 13 gallons of liquid were maintained by a level controller controlling the reactor outlet flow. The reactor was maintained at 65° C. by an external cooler in a product recirculating loop. The residence time based on the total feed rate and the reactor liquid volume was 38 minutes. The outlet hydrolyzate sample, based on a gas chromatographic analysis, was found to contain less than 0.1% nitrile, 34.9% amide, and 11.2% HMBA. The outlet stream was introduced to the second 30 gallon CSTR having a liquid volume of 27.7 gallons. An 80° C. hot water stream was also fed to the second CSTR at a rate of 60.5 lbs/hr. The reactor temperature was 105° C. and the residence time was 91 minutes. The hydrolyzate from the reactor contained 1.9% amide, indicating that more than 90% of incoming amide was converted to HMBA in this vessel. The second CSTR outlet stream then entered the packed column reactor containing structure packing and having a total liquid volume of 25 gallons. From the various samples obtained along the length of the column reactor, the amide hydrolysis reaction was found to have approached completion at 70% of the length of the reactor. The temperature profile of the adiabatic column reactor ranged from 100 to 102° C. and the residence time in the PFR was 52.9 minutes. The final product contained less than 0.1% nitrile, less than 0.1% amide, and 48% HMBA. The major by-product of the hydrolysis process, ammonium bisulfate, can be separated from the product by conventional means.

EXAMPLE 23

The equipment as used in Example 22 was used for the following hydrolysis process except that the second CSTR was bypassed such that the packed column reactor was the sole reactor for the amide hydrolysis reaction (FIG. 2).

The feed rates to the first CSTR were as described in Example 22. However, the temperature in the first CSTR was 60° C. Analysis of the outlet sample revealed that the intermediate hydrolysis solution contained 0.2% nitrile, 39.4% amide, and 9.5% HMBA. The lower CSTR operating temperature resulted in a slightly higher nitrile concentration but a lower HMBA concentration. The intermediate hydrolysis solution was mixed with a hot water stream (60.5 lbs/hr) in an in-line static mixer. The diluted aqueous hydrolysis solution entered the PFR which maintained a steady state temperature profile from 80° C. at the inlet, reaching a peak temperature of 105° C. at the middle and dropping to 102° C. at the outlet of the packed column. Although the column walls were heat traced and insulated, some heat losses were encountered. The residence time in the column reactor was 52.9 minutes. The final hydrolyzate at the outlet of the column reactor contained less than 0.1% nitrile, 0.1% amide and 40.8% HMBA, the balance being by-product ammonium bisulfate and water.

EXAMPLE 24

The equipment as utilized in Example 23 was used in the following hydrolysis except that concentrated sulfuric acid was fed directly to the first CSTR (FIG. 3) without pre-dilution to 65% sulfuric acid with water. A water stream was also fed to the reactor. Thus, both the heat of dilution of the acid and the heat of hydrolysis were removed via the external circulating cooler. The second CSTR was by-passed.

Nitrile (72 lbs/hr), 96% sulfuric acid (56.2 lbs/hr) and dilution water (26.7 lbs/hr) were simultaneously fed to the first CSTR where nitrile hydrolysis was occurring. The operating liquid volume was 10 gallons, which provided 42.5 minutes of residence time based on the total sum of the three feed rates. The reaction temperature was controlled at 55° C. The gas chromatographic analysis of the intermediate hydrolysis solution showed that it contained 0.5% nitrile, 40.6% amide, and 5.7% HMBA. The intermediate hydrolysis solution was mixed with 41.3 lbs/hr hot water in the in-line static mixer. The diluted aqueous hydrolysis solution entered the packed column reactor in the same fashion as described in Example 23, except that the adiabatic reaction temperatures in the column reactor were slightly higher, probably due to additional heat release from the higher unreacted nitrile content leaving the CSTR which was operated at a lower temperature. From the samples withdrawn from the column reactor, the amide hydrolysis was determined to have been completed at 70% of the column height from the bottom inlet.

EXAMPLES 25–38

Hydrolysis solution samples were taken at the outlet of each CSTR, the PFR inlet (S1), the PFR outlet (S6), and at four sampling ports along the length of the PFR (S2 through S5) as shown in FIG. 2. The samples were removed during steady state conditions and were analyzed by a gas chromatographic method to determine the hydrolysis solution composition when leaving the CSTRs and when flowing through the PFR. The hydrolysis solution composition and the temperature and residence time in each CSTR and within each section of the PFR are shown below. The remainder of the hydrolysis solution included water and ammonium bisulfate. Examples which do not indicate CSTR-II data involved equipment wherein the second CSTR was bypassed such that a diluted aqueous hydrolysis solution flowed from the in-line mixer directly to the PFR.

The data demonstrate that conversion is affected by temperature, acid/nitrile ratio and the degree of axial back-mixing in the plug flow reactor. Backmixing is in turn a function of the velocity at which the reacting mixture flows through the reactor. In the instances in which backmixing affected conversion, the reactor was operated at less than its threshold velocity of 1.0 mm/sec., resulting in a lower average driving force, i.e., amide concentration integrated along the length of the reactor, for this non-zero order reaction. In some instances, it was possible to compensate for operation below threshold velocity using relatively higher temperature and/or acid/nitrile ratio. Further discussion of the relationship of velocity to axial back-mixing and the resultant effect on conversion is set forth at the end of Example 38.

EXAMPLE 25

Nitrile at 105.00 lbs/hr was fed to the first CSTR, along with 120.95 lbs/hr 65% sulfuric acid, giving a 1.03 acid/nitrile molar ratio. A water feed at 60.50 lbs/hr was also introduced into the second CSTR. The hydrolysis solution composition for each sample and the temperature and residence time for each location are shown in Table 20 below.

TABLE 20

| | CSTR-I | CSTR-II | S1 | S2 | S3 | S4 | S5 | S6 |
|---|---|---|---|---|---|---|---|---|
| Volume (gal) | 13 | 27.7 | | | 17.5 (total PFR) | | | |
| Temperature (° C.) | 65 | 104 | 101 | 103 | 102 | 103 | 103 | 102 |
| Residence Time (min) | | | | | | | | |
| Hydrolysis Solution Composition (wt. %) | | | | | | | | |
| Nitrile | 0.02 | 0.02 | 0.01 | 0.01 | 0.02 | trace | trace | trace |
| HMBA | 12 | 41 | 34 | 39 | 39 | 39 | 41 | 40 |
| Amide | 34 | 2.0 | 0.5 | 0.27 | 0.04 | 0.02 | 0.02 | 0.02 |

PFR Velocity = 1.0 mm/sec.
Hydrolyzate Product Color: 11–12 on Gardner scale

EXAMPLE 26

Nitrile at 105.00 lbs/hr was fed to the first CSTR, along with 120.95 lbs/hr 65% sulfuric acid, giving a 1.00 acid/nitrile molar ratio. A water feed at 60.50 lbs/hr was also introduced into the second CSTR. The hydrolysis solution composition for each sample and the temperature and residence time for each location are shown in Table 21 below.

TABLE 21

| | CSTR-I | CSTR-II | S1 | S2 | S3 | S4 | S5 | S6 |
|---|---|---|---|---|---|---|---|---|
| Volume (gal) | 13 | 27.7 | | | 17.5 (total PFR) | | | |
| Temperature (° C.) | 65 | 105 | 101 | 102 | 102 | 102 | 102 | 101 |
| Residence Time (min) | | | | | | | | |
| Hydrolysis Solution Composition (wt. %) | | | | | | | | |
| Nitrile | 0.01 | trace | trace | trace | trace | trace | trace | 0.01 |
| HMBA | 11 | 36 | 37 | 29 | 26 | 30 | 31 | 47 |
| Amide | 35 | 1.9 | 1.1 | 0.21 | 0.05 | 0.05 | 0.05 | 0.05 |

PFR Velocity = 1.0 mm/sec.
Hydrolyzate Product Color: 6–7 on Gardner scale

EXAMPLE 27

Nitrile at 105.00 lbs/hr was fed to the first CSTR, along with 145.14 lbs/hr 65% sulfuric acid, giving a 1.21 acid/nitrile molar ratio. A water feed at 57.4 lbs/hr was also introduced into the second CSTR. The hydrolysis solution composition for each sample and the temperature and residence time for each location are shown in Table 22 below.

TABLE 22

|  | CSTR-I | CSTR-II | S1 | S2 | S3 | S4 | S5 | S6 |
|---|---|---|---|---|---|---|---|---|
| Volume (gal) | 13 | 27.7 |  |  | 17.5 (total PFR) |  |  |  |
| Temperature (° C.) | 65 | 93 | 90 | 93 | 92 | 92 | 92 | 91 |
| Residence Time (min) |  |  |  |  |  |  |  |  |
| Hydrolysis Solution Composition (wt. %) | | | | | | | | |
| Nitrile | trace | trace | trace | trace | trace | trace | trace | trace |
| HMBA | 11 | 33 | 34 | 35 | 36 | 36 | 38 | 33 |
| Amide | 31 | 1.8 | 1.3 | 0.14 | 0.02 | 0.01 | 0.01 | 0.01 |

PFR Velocity = 1.0 mm/sec.
Hydrolyzate Product Color: 9–10 on Gardner scale

EXAMPLE 28

Nitrile at 72.00 lbs/hr was fed to the first CSTR, along with 82.94 lbs/hr 65% sulfuric acid, giving a 1.0 acid/nitrile molar ratio. A water feed at 41.30 lbs/hr was also introduced into the in-line mixer. The hydrolysis solution composition for each sample and the temperature and residence time for each location are shown in Table 23 below.

TABLE 23

|  | CSTR-I | S1 | S2 | S3 | S4 | S5 | S6 |
|---|---|---|---|---|---|---|---|
| Volume (gal) | 10 |  |  | 19.9 (total PFR) |  |  |  |
| Temperature (° C.) | 65 | 80 | 96 | 97 | 97 | 97 | 97 |
| Residence Time (min) |  |  |  |  |  |  |  |
| Hydrolysis Solution Composition (wt. %) | | | | | | | |
| Nitrile | 0.13 | 0.03 | 0.02 | 0.01 | 0.01 | 0.01 | 0.02 |
| HMBA | 14 | 22 | 28 | 24 | 27 | 25 | 44 |
| Amide | 40 | 19 | 3.3 | 1.6 | 1.7 | 1.4 | 1.2 |

PFR Velocity = 0.69 mm/sec.
Hydrolyzate Product Color: 3 on Gardner scale

EXAMPLE 29

Nitrile at 72.00 lbs/hr was fed to the first CSTR, along with 82.94 lbs/hr 65% sulfuric acid, giving a 1.0 acid/nitrile molar ratio. A water feed at 41.30 lbs/hr was also introduced into the in-line mixer. The hydrolysis solution composition for each sample and the temperature and residence time for each location are shown in Table 24 below.

TABLE 24

|  | CSTR-I | S1 | S2 | S3 | S4 | S5 | S6 |
|---|---|---|---|---|---|---|---|
| Volume (gal) | 10 |  |  | 19.9 (total PFR) |  |  |  |
| Temperature (° C.) | 60 | 81 | 103 | 103 | 101 | 101 | 100 |
| Residence Time (min) |  |  |  |  |  |  |  |
| Hydrolysis Solution Composition (wt. %) | | | | | | | |
| Nitrile | 0.19 | 0.01 | trace | trace | trace | trace | trace |
| HMBA | 8.8 | 20 | 38 | 37 | 39 | 47 | 54 |
| Amide | 38 | 22 | 1.4 | 0.59 | 0.34 | 0.33 | 0.06 |

PFR Velocity = 0.69 mm/sec.
Hydrolyzate Product Color: 6–7 on Gardner scale

EXAMPLE 30

Nitrile at 150.00 lbs/hr was fed to the first CSTR, along with 172.79 lbs/hr 65% sulfuric acid, giving a 1.04 acid/nitrile molar ratio. A water feed at 86.40 lbs/hr was also introduced into the second CSTR. The hydrolysis solution composition for each sample and the temperature and residence time for each location are shown in Table 25 below.

TABLE 25

|  | CSTR-I | CSTR-II | S1 | S2 | S3 | S4 | S5 | S6 |
|---|---|---|---|---|---|---|---|---|
| Volume (gal) | 10 | 27.7 |  |  | 25.0 (total PFR) |  |  |  |
| Temperature (° C.) | 65 | 104 | 100 | 102 | 102 | 102 | 102 | 101 |
| Residence Time (min) |  |  |  |  |  |  |  |  |
|  |  | Hydrolysis Solution Composition (wt. %) | | | | | | |
| Nitrile | 0.26 | 0.03 | 0.01 | trace | trace | trace | trace | trace |
| HMBA | 8.1 | 35 | 37 | 39 | 37 | 37 | 39 | 38 |
| Amide | 38 | 3.0 | 1.5 | 0.21 | 0.03 | 0.02 | 0.02 | 0.02 |

PFR Velocity = 1.4 mm/sec.
Hydrolyzate Product Color: 10–11 on Gardner scale

EXAMPLE 31

Nitrile at 150.00 lbs/hr was fed to the first CSTR, along with 172.79 lbs/hr 65% sulfuric acid, giving a 1.02 acid/nitrile molar ratio. A water feed at 86.40 lbs/hr was also introduced into the second CSTR. The hydrolysis solution composition for each sample and the temperature and residence time for each location are shown in Table 26 below.

TABLE 26

|  | CSTR-I | CSTR-II | S1 | S2 | S3 | S4 | S5 | S6 |
|---|---|---|---|---|---|---|---|---|
| Volume (gal) | 10 | 27.7 |  |  | 25.0 (total PFR) |  |  |  |
| Temperature (° C.) | 65 | 102 | 100 | 103 | 103 | 104 | 103 | 102 |
| Residence Time (min) |  |  |  |  |  |  |  |  |
|  |  | Hydrolysis Solution Composition (wt. %) | | | | | | |
| Nitrile | 0.13 | 0.01 | 0.03 | 0.03 | 0.02 | 0.02 | 0.02 | 0.01 |
| HMBA | 7.0 | 36 | 37 | 39 | 39 | 40 | 41 | 40 |
| Amide | 40 | 3.2 | 2.4 | 0.84 | 0.23 | 0.18 | 0.16 | 0.13 |

PFR Velocity = 1.4 mm/sec.
Hydrolyzate Product Color: 8–9 on Gardner scale

EXAMPLE 32

Nitrile at 105.00 lbs/hr was fed to the first CSTR, along with 120.95 lbs/hr 65% sulfuric acid, giving a 1.02 acid/nitrile molar ratio. A water feed at 60.50 lbs/hr was also introduced into the second CSTR. The hydrolysis solution composition for each sample and the temperature and residence time for each location are shown in Table 27 below.

TABLE 27

|  | CSTR-I | CSTR-II | S1 | S2 | S3 | S4 | S5 | S6 |
|---|---|---|---|---|---|---|---|---|
| Volume (gal) | 10 | 27.7 |  |  | 17.5 (total PFR) |  |  |  |
| Temperature (° C.) | 63 | 105 | 101 | 103 | 103 | 103 | 103 | 101 |
| Residence Time (min) |  |  |  |  |  |  |  |  |
|  |  | Hydrolysis Solution Composition (wt. %) | | | | | | |
| Nitrile | 0.36 | 0.03 | 0.01 | 0.01 | 0.01 | trace | trace | trace |
| HMBA | 9.1 | 38 | 38 | 40 | 40 | 41 | 39 | 40 |
| Amide | 39 | 2.7 | 1.8 | 0.32 | 0.08 | 0.05 | 0.05 | 0.03 |

PFR Velocity = 1.0 mm/sec.
Hydrolyzate Product Color: 10–11 on Gardner scale

EXAMPLE 33

Nitrile at 72.00 lbs/hr was fed to the first CSTR, along with 82.94 lbs/hr 65% sulfuric acid, giving a 1.0 acid/nitrile molar ratio. A water feed at 41.30 lbs/hr was also introduced into the in-line mixer. The hydrolysis solution composition for each sample and the temperature and residence time for each location are shown in Table 28 below.

TABLE 28

|  | CSTR-I | S1 | S2 | S3 | S4 | S5 | S6 |
|---|---|---|---|---|---|---|---|
| Volume (gal) | 10 | | | 19.9 (total PFR) | | | |
| Temperature (° C.) | 60 | 84 | 103 | 105 | 105 | 105 | 103 |
| Residence Time (min) | | | | | | | |
| Hydrolysis Solution Composition (wt. %) | | | | | | | |
| Nitrile | 0.41 | 0.02 | 0.01 | 0.01 | 0.01 | 0.01 | 0.01 |
| HMBA | 9.5 | 23 | 26 | 23 | 23 | 23 | 47 |
| Amide | 43 | 17 | 2.3 | 0.63 | 0.62 | 0.61 | 0.72 |

PFR Velocity = 0.69 mm/sec.
Hydrolyzate Product Color: 5–6 on Gardner scale

EXAMPLE 34

Nitrile at 90.60 lbs/hr was fed to the first CSTR, along with 103.80 lbs/hr 65% sulfuric acid, giving a 1.03 acid/nitrile molar ratio. A water feed at 51.90 lbs/hr was also introduced into the in-line mixer. The hydrolysis solution composition for each sample and the temperature and residence time for each location are shown in Table 29 below.

TABLE 29

|  | CSTR-I | S1 | S2 | S3 | S4 | S5 | S6 |
|---|---|---|---|---|---|---|---|
| Volume (gal) | 12.6 | | | 25.0 (total PFR) | | | |
| Temperature (° C.) | 59 | 82 | 104 | 105 | 105 | 105 | 104 |
| Residence Time (min) | | | | | | | |
| Hydrolysis Solution Composition (wt. %) | | | | | | | |
| Nitrile | 0.39 | 0.03 | 0.01 | 0.01 | 0.01 | 0.01 | 0.01 |
| HMBA | 9.1 | 23 | 33 | 30 | 31 | 31 | 38 |
| Amide | 41 | 18 | 2.0 | 0.92 | 0.79 | 0.71 | 0.76 |

PFR Velocity = 0.69 mm/sec.
Hydrolyzate Product Color: 8–9 on Gardner scale

EXAMPLE 35

Nitrile at 90.60 lbs/hr was fed to the first CSTR, along with 124.80 lbs/hr 65% sulfuric acid, giving a 1.20 acid/nitrile molar ratio. A water feed at 49.40 lbs/hr was also introduced into the in-line mixer. The hydrolysis solution composition for each sample and the temperature and residence time for each location are shown in Table 30 below.

TABLE 30

|  | CSTR-I | S1 | S2 | S3 | S4 | S5 | S6 |
|---|---|---|---|---|---|---|---|
| Volume (gal) | 12.6 | | | 25.0 (total PFR) | | | |
| Temperature (° C.) | 45 | 86 | 107 | 107 | 107 | 107 | 105 |
| Residence Time (min) | | | | | | | |
| PFR Velocity = 0.86 mm/sec. | | | | | | | |
| Hydrolysis Solution Composition (wt. %) | | | | | | | |
| Nitrile | 0.07 | 0.01 | trace | trace | trace | trace | trace |
| HMBA | 8.1 | 23 | 35 | 33 | 39 | 37 | 37 |
| Amide | 36 | 12 | 1.0 | trace | trace | trace | 0.01 |

Hydrolyzate Product Color: 11–12 on Gardner scale

EXAMPLE 36

Nitrile at 90.60 lbs/hr was fed to the first CSTR, along with 124.80 lbs/hr 65% sulfuric acid, giving a 1.20 acid/nitrile molar ratio. A water feed at 49.40 lbs/hr was also introduced into the in-line mixer. The hydrolysis solution composition for each sample and the temperature and residence time for each location are shown in Table 31 below.

TABLE 31

|  | CSTR-I | S1 | S2 | S3 | S4 | S5 | S6 |
|---|---|---|---|---|---|---|---|
| Volume (gal) | 12.6 | | | 25.0 (total PFR) | | | |
| Temperature (° C.) | 58 | 82 | 105 | 103 | 103 | 103 | 101 |
| Residence Time (min) | | | | | | | |
| Hydrolysis Solution Composition (wt. %) | | | | | | | |
| Nitrile | trace | trace | trace | trace | trace | trace | trace |
| HMBA | 8.3 | 20 | 38 | 37 | 38 | 38 | 39 |
| Amide | 31 | 18 | 0.96 | trace | trace | trace | trace |

PFR Velocity = 0.86 mm/sec.
Hydrolyzate Product Color: 11–12 on Gardner scale

EXAMPLE 37

Nitrile at 90.60 lbs/hr was fed to the first CSTR, along with 103.80 lbs/hr 65% sulfuric acid, giving a 1.0 acid/nitrile molar ratio. A water feed at 51.90 lbs/hr was also introduced into the in-line mixer. The hydrolysis solution composition for each sample and the temperature and residence time for each location are shown in Table 32 below.

TABLE 32

| | CSTR-I | S1 | S2 | S3 | S4 | S5 | S6 |
|---|---|---|---|---|---|---|---|
| Volume (gal) | 12.6 | | | 25.0 (total PFR) | | | |
| Temperature (° C.) | 59 | 88 | 109 | 109 | 109 | 109 | 107 |
| Residence Time (min) | | | | | | | |
| Hydrolysis Solution Composition (wt. %) | | | | | | | |
| Nitrile | 0.09 | 0.01 | trace | 0.01 | trace | trace | 0.01 |
| HMBA | 8.8 | 26 | 38 | 69 | 38 | 40 | 41 |
| Amide | 37 | 13 | 0.30 | 0.02 | 0.01 | 0.01 | trace |

PFR Velocity = 0.86 mm/sec.
Hydrolyzate Product Color: 11–12 on Gardner scale

EXAMPLE 38

Nitrile at 105.00 lbs/hr was fed to the first CSTR, along with 120.95 lbs/hr 65% sulfuric acid, giving a 1.0 acid/nitrile molar ratio. A water feed at 60.50 lbs/hr was also introduced into the in-line mixer. The hydrolysis solution composition for each sample and the temperature and residence time for each location are shown in Table 33 below.

TABLE 33

| | CSTR-I | S1 | S2 | S3 | S4 | S5 | S6 |
|---|---|---|---|---|---|---|---|
| Volume (gal) | 14.6 | | | 25.0 (total PFR) | | | |
| Temperature (° C.) | 60 | 80 | 103 | 104 | 105 | 104 | 102 |
| Residence Time (min) | | | | | | | |
| Hydrolysis Solution Composition (wt. %) | | | | | | | |
| Nitrile | 0.22 | 0.02 | 0.01 | 0.01 | 0.01 | 0.01 | 0.01 |
| HMBA | 9.5 | 24 | 39 | 45 | 45 | 42 | 41 |
| Amide | 39 | 21 | 2.5 | 0.19 | 0.20 | 0.28 | 0.11 |

PFR Velocity = 1.0 mm/sec.
Hydrolyzate Product Color: 8–9 on Gardner scale

As noted above, certain of the conversions obtained in a packed column PFR were not sufficient to meet target residual amide concentrations in the product hydrolyzate. These lower conversions were attributable to lower reaction temperature or acid/nitrile ratio, excessive axial backmixing, or some combination of these factors. Based on studies conducted on reactors operated at velocity adequate to provide a Peclet number greater than about 50, it was determined that residual amide concentration in the hydrolyzate could be consistently reduced to less than about 0.03% at reaction temperatures and acid/nitrile ratios in the preferred ranges discussed above for steady state operations. But where the Peclet number was significantly below 50, lower conversions were generally found unless temperature and/or acid/nitrile ratio were increased to compensate.

To investigate the effect of velocity on back-mixing in a packed column PFR, residence time distribution tests were conducted at varying velocities using a pulse of salt as a tracer injected at the bottom of a column in which tap water was caused to flow upwardly. At the top outlet of the reactor a conductivity probe was inserted for measuring the conductivity of the outlet flow, from which tracer response data, in terms of salt (NaCl) concentration vs. time, were obtained. Following conventional methods, calculations based on the response data were made to determine the mean residence time (the first moment of distribution), the variance (the second moment of distribution), the Peclet number, and the equivalent number of stirred tanks in series. For the reactor tested, the flow rate (gpm), mean residence time ($\Theta$), dimensionless variance ($\sigma^2$), Peclet number (Pe), and number of equivalent stirred tank reactors (j), are set forth in Table 34.

TABLE 34

| gpm | $\Theta$ | $\sigma^2$ | Pe | j |
|---|---|---|---|---|
| 0.95 | 29.5 | 0.0393 | 50.9 | 25.5 |
| 0.47 | 66.3 | 0.0681 | 29.4 | 14.7 |
| 0.90 | 25.1 | 0.0749 | 26.7 | 13.4* |

*Based on injection of tracer at a port spaced above the bottom of the reactor. Adjusted for this factor, j = 20.5 and Pe = 41.

These data demonstrate a critical velocity threshold in the range of 0.5 gpm for the packed column that was used in these tests.

Based on kinetic calculations on the amide hydrolysis reaction, the relationship between the number of equivalent stirred tank reactors and the residual amide concentration was calculated. Computations were also made of the correlation between the number of equivalent stirred tank reactors and: (a) the ratio of (requisite reactor length for a given degree of conversion) to (requisite length for the same degree of conversion under perfect plug flow conditions) ($L/L_p$); and (b) the ratio between (residual amide concentration for a given length of reactor) vs. (residual amide concentration for the same length reactor under perfect plug flow conditions) ($C/C_p$). These calculations are set forth in Table 35.

TABLE 35

| j | $L/L_p$ | $C/C_p$ | C (% amide out) |
|---|---|---|---|
| 15 | 1.236 | 2.66 | 0.0581% |
| 20 | 1.177 | 2.25 | 0.0491 |
| 25 | 1.141 | 2.00 | 0.0436 |
| 30 | 1.178 | 1.83 | 0.0399 |
| 40 | 1.088 | 1.62 | 0.0353 |
| ∞ | 1.000 | 1.00 | 0.0218 |

While the invention is susceptible to various modifications and alternative forms, specific embodiments thereof have been shown by way of example in the drawings and have been described herein in detail. It should be understood, however, that it is not intended to limit the invention to the particular form disclosed, but on the contrary, the intention is to cover all modifications, equivalents and alternatives falling within the spirit and scope of the invention as defined by the appended claims.

We claim:

1. A process for the preparation of 2-hydroxy-4-methylthiobutanoic acid comprising:
   introducing sulfuric acid into a first reactor comprising a continuous stirred tank reactor;
   introducing 2-hydroxy-4-methylthiobutanenitrile into said first reactor, the molar ratio of sulfuric acid to 2-hydroxy-4-methylthiobutanenitrile introduced into said first reactor being between about 0.6 to about 1.5;
   continuously hydrolyzing 2-hydroxy-4-methylthiobutyronitrile within said first reactor at a temperature less than about 70° C. to produce an intermediate aqueous hydrolysis solution containing 2-hydroxy-4-methylthiobutanamide;
   continuously introducing water and the intermediate aqueous hydrolysis solution into a plug flow reactor; and
   continuously hydrolyzing 2-hydroxy-4-methylthiobutanamide within said plug flow reactor to produce an aqueous hydrolyzate product solution containing 2-hydroxy-4-methylthiobutanoic acid.

2. The process as set forth in claim 1 wherein the molar ratio of sulfuric acid to 2-hydroxy-4-methylthiobutanenitrile introduced into the first reactor is between about 0.9 and about 1.2.

3. The process as set forth in claim 1 wherein the molar ratio of sulfuric acid to 2-hydroxy-4-methylthiobutanenitrile introduced into the first reactor is between about 1.0 and about 2.0 during the period between start up of the process until steady state conditions are established in the plug flow reactor, and thereafter said molar ratio of sulfuric acid to 2-hydroxy-4-methylthiobutanenitrile introduced into said first reactor being between about 0.6 and about 1.5.

4. The process as set forth in claim 1 wherein the molar ratio of sulfuric acid to 2-hydroxy-4-methylthiobutanenitrile introduced into the first reactor is between about 1.0 and about 1.5 during the period between start up of the process until steady state conditions are established in the plug flow reactor, and thereafter said molar ration of sulfuric acid to 2-hydroxy-4-methylthiobutanenitrile introduced into said first reactor being between about 0.9 and about 1.2.

5. The process of claim 1 wherein 2-hydroxy-4-methylthiobutyronitrile is continuously hydrolyzed within said first reactor at a temperature between about 40° C. to about 70 ° C. to produce an intermediate aqueous hydrolysis solution containing 2-hydroxy-4-methylthiobutanamide.

6. The process of claim 1 wherein 2-hydroxy-4-methylthiobutyronitrile is continuously hydrolyzed within said first reactor at a temperature between about 55° C. to about 65° C. to produce an intermediate aqueous hydrolysis solution containing 2-hydroxy-4-methylthiobutanamide.

7. The process of claim 1 wherein 2-hydroxy-4-methylthiobutyronitrile is continuously hydrolyzed within said first reactor at a temperature between about 60° C. to about 65° C. to produce an intermediate aqueous hydrolysis solution containing 2-hydroxy-4-methylthiobutanamide.

* * * * *